(12) United States Patent
Stamp

(10) Patent No.: US 7,645,265 B2
(45) Date of Patent: Jan. 12, 2010

(54) INJECTION DEVICE

(75) Inventor: Kevin Stamp, Sheffield (GB)

(73) Assignee: The Medical House PLC (GB)

( * ) Notice: Subject to any disclaimer, the term of this patent is extended or adjusted under 35 U.S.C. 154(b) by 211 days.

(21) Appl. No.: 10/597,379

(22) PCT Filed: Jan. 24, 2005

(86) PCT No.: PCT/GB2005/000223

§ 371 (c)(1),
(2), (4) Date: Jul. 21, 2006

(87) PCT Pub. No.: WO2005/070481

PCT Pub. Date: Aug. 4, 2005

(65) Prior Publication Data

US 2008/0228143 A1 Sep. 18, 2008

(30) Foreign Application Priority Data

Jan. 23, 2004 (GB) ................................. 0401469.2
Jan. 27, 2004 (CA) .................................... 2455937

(51) Int. Cl.
*A61M 5/20* (2006.01)
(52) U.S. Cl. ..................... 604/136; 604/134; 604/156; 604/162; 604/157; 604/187; 604/192; 604/196; 604/197; 606/167; 606/181
(58) Field of Classification Search ................ 604/134, 604/136, 156, 157, 162, 187, 197, 196, 192; 606/167, 181
See application file for complete search history.

(56) References Cited

U.S. PATENT DOCUMENTS 3,702,608 A * 11/1972 Tibbs ......................... 604/136

(Continued)

FOREIGN PATENT DOCUMENTS

EP 0453212 4/1991

(Continued)

OTHER PUBLICATIONS

UK Search Report for Application No. GB0602411.1, Apr. 6, 2006.
Corrected Search Report under Section 17, GB0620163.6, Nov. 24, 2006, Mr. Jeremy Cowen, 1 page.

(Continued)

*Primary Examiner*—Nicholas D Lucchesi
*Assistant Examiner*—Scott Medway
(74) *Attorney, Agent, or Firm*—Sheridan Ross P.C.

(57) ABSTRACT

An injection device comprising an outer housing inside which is located a medicament-holding barrel (9) with a needle (10) at one end thereof, at least part of the needle being moveable in and out of the outer housing, a plunger (8) moveable within the barrel, an inner housing (7) intermediate the outer housing (6) and the barrel and plunger and an energy source (1) in communication with said inner housing. The inner housing is moveable by the energy source between a first position in which the plunger and barrel are movable axially so as to move at least part of said needle out of the outer housing; a second position in which the plunger is movable axially into said barrel so as to expel medicament through the needle; and a third position in which the plunger and barrel are able to retract in order to retract the needle into the outer housing.

31 Claims, 27 Drawing Sheets

U.S. PATENT DOCUMENTS

| | | | |
|---|---|---|---|
| 3,797,489 A * | 3/1974 | Sarnoff | 604/136 |
| 3,811,442 A | 5/1974 | Maroth | |
| 4,617,016 A | 10/1986 | Blomberg | |
| 4,913,699 A | 4/1990 | Parsons | |
| 4,958,622 A * | 9/1990 | Selenke | 600/578 |
| 4,976,724 A * | 12/1990 | Nieto et al. | 606/181 |
| 5,024,656 A | 6/1991 | Gasaway et al. | |
| 5,042,977 A * | 8/1991 | Bechtold et al. | 604/134 |
| 5,078,698 A | 1/1992 | Stiehl et al. | |
| 5,167,632 A * | 12/1992 | Eid et al. | 604/136 |
| 5,211,625 A * | 5/1993 | Sakurai et al. | 604/22 |
| 5,300,030 A * | 4/1994 | Crossman et al. | 604/136 |
| 5,478,316 A | 12/1995 | Bitdinger et al. | |
| 5,599,309 A * | 2/1997 | Marshall et al. | 604/136 |
| 5,634,906 A * | 6/1997 | Haber et al. | 604/136 |
| 5,658,261 A | 8/1997 | Neer et al. | |
| 5,681,291 A | 10/1997 | Galli | |
| 5,779,675 A | 7/1998 | Reilly et al. | |
| 5,779,677 A * | 7/1998 | Frezza | 604/134 |
| 6,210,369 B1 * | 4/2001 | Wilmot et al. | 604/157 |
| 6,264,629 B1 | 7/2001 | Landau | |
| 6,270,479 B1 * | 8/2001 | Bergens et al. | 604/156 |
| 6,280,421 B1 | 8/2001 | Kirchhofer et al. | |
| 6,544,234 B1 | 4/2003 | Gabriel | |
| 6,620,137 B2 | 9/2003 | Kirchhofer et al. | |
| 6,752,781 B2 | 6/2004 | Landau et al. | |
| 7,156,823 B2 | 1/2007 | Landau et al. | |
| 2001/0004681 A1 | 6/2001 | Landau | |
| 2001/0053886 A1 | 12/2001 | Caizza | |
| 2003/0000524 A1 | 1/2003 | Anderson et al. | |
| 2003/0045858 A1 | 3/2003 | Struys et al. | |
| 2003/0093030 A1 | 5/2003 | Landau | |
| 2003/0105430 A1* | 6/2003 | Lavi et al. | 604/136 |
| 2005/0165349 A1 | 7/2005 | Stamp | |
| 2005/0165360 A1 | 7/2005 | Stamp | |
| 2007/0173770 A1 | 7/2007 | Stamp | |

FOREIGN PATENT DOCUMENTS

| | | |
|---|---|---|
| EP | 0518416 | 12/1992 |
| EP | 1323477 | 7/2003 |
| EP | 1323447 | 8/2003 |
| GB | 886444 | 1/1962 |
| GB | 2396298 | 6/2004 |
| GB | 2410188 | 7/2005 |
| WO | WO 99/22792 | 5/1999 |
| WO | 0009186 | 2/2000 |
| WO | WO 01/93926 | 12/2001 |
| WO | WO 02/070051 | 9/2002 |
| WO | 03097133 | 11/2003 |
| WO | WO 03/099358 | 12/2003 |
| WO | WO 2005/070481 | 8/2005 |
| WO | 2005/097252 | 10/2005 |
| WO | WO 2005/115507 | 12/2005 |
| WO | WO 2006/106291 | 10/2006 |
| WO | WO 2006/106295 | 10/2006 |

OTHER PUBLICATIONS

Official Action for U.S. Appl. No. 10/767,859, mailed Feb. 24, 2006.
Official Action for U.S. Appl. No. 10/767,859, mailed Sep. 12, 2006.
Official Action for U.S. Appl. No. 10/767,859, mailed Jun. 5, 2007.
Official Action for U.S. Appl. No. 10/767,860, mailed Mar. 14, 2006.
Official Action for U.S. Appl. No. 10/767,860, mailed Aug. 22, 2006.
Official Action for U.S. Appl. No. 10/767,860, mailed Apr. 10, 2007.
Official Action for U.S. Appl. No. 10/767,860, mailed Sep. 24, 2007.
Official Action for U.S. Appl. No. 10/767,860, mailed Jan. 11, 2008, 8 pages.
Official Action for U.S. Appl. No. 10/767,859, mailed Dec. 28, 2007, 8 pages.
PCT Written Opinion of the International Searching Authority corresponding to International Application No. PCT/GB2005/000223, Jun. 22, 2005, 7 pages.
Official Action for U.S. Appl. No. 10/767,860, mailed Dec. 15, 2006, 3 pages.
PCT International Preliminary Report on Patentability dated Jan. 23, 2006 for Application No. PCT/GB2005/000223.
Official Action for U.S. Appl. No. 10/767,860, mailed Jun. 12, 2008, pp. 1-4.
U.S. Appl. No. 12/161,776, Stamp (Jul. 22, 2008).
International Search Report for International (PCT) Patent Application No. PCT/GB2007/000141, mailed May 5, 2007, pp. 1-2.
Written Opinon for International (PCT) Patent Application No. PCT/GB2007/000141, mailed May 5, 2007, pp. 1-7.
Authorized Officer Mulhausen, International Preliminary Report on Patentability for International (PCT) Patent Application No. PCT/GB2007/000141, dated Jul. 29, 2008.
UK Search Report for Application No. GB0620163.6, dated Nov. 24, 2006, 1 page.
Advisory Action for U.S. Appl. No. 10/767,860, mailed Sep. 5, 2008, 3 pages.
Interview Summary for U.S. Appl. No. 10/767,860, mailed Feb. 2, 2009, 4 pages.
Official Action for U.S. Appl. No. 10/767,860, mailed Dec. 2, 2008, 5 pages.
Restriction Requirement for U.S. Appl. No. 11/387,645, mailed May 28, 2009, 7 pages.

* cited by examiner

INJECTION DEVICE

CROSS REFERENCE TO RELATED APPLICATION

This application is a national stage application under 35 U.S.C. 371 of PCT Application No. PCT/GB2005/000223 having an international filing date of Jan. 24, 2005, which designated the United States, which PCT application claimed the benefit of United Kingdom Application Serial No. 0401469.2, filed Jan. 23, 2004; Canada Application Serial No. 2,455,937, filed Jan. 27, 2004; and U.S. patent application Ser. No. 10/767,860, filed Jan. 28, 2004, the entire disclosures of which are hereby incorporated herein by reference.

This invention relates to the field of injection devices for the administration of liquid medication, for example, insulin or growth hormone.

One type of injection device is known as a mini-needle or micro-needle device. These devices comprise a pressurised ("forced") injection system and have a needle which is shorter than that of conventional needle systems. The needle is normally hidden which is advantageous both for avoiding needle stick injuries and for minimising trauma to needle-phobic patients. The needle is hidden both before and after the injection is delivered, appearing only for the duration of the injection. Mini needle devices can typically deliver a larger volume of medication than needle-free devices and can deliver faster than conventional needle systems.

One such known device is described in WO00/09186 (MediJect Corporation) for "Needle assisted jet injector" and this document gives a useful summary of prior art devices.

The device of WO 00/09186 includes a needle which is, in one embodiment, retractably located within an injector nozzle assembly. Upon activation of a force generating source, a portion of the needle extends past the nozzle assembly and penetrates the outer layer of skin to deliver medicament via jet injection to a deeper region. After activation, the needle retracts back into the nozzle assembly. The retractable needle is housed within the nozzle and is pushed forward so that it emerges in order to deliver an injection by the liquid medicament itself, when the medicament is itself pushed forward by the plunger.

Although the present invention may relate to mini-needle or jet injection devices, the invention is equally applicable to other types of injection device, for example those for deep-penetrating muscular injection as well as those which are for shallower, subcutaneous, injection.

According to a first aspect of the present invention there is provided an injection device comprising an outer housing inside which is located
  a barrel for holding a volume of a medicament;
  a needle at one end of the barrel, the needle and barrel being such that at least part of the needle is axially moveable in and out of said outer housing but is biased to be normally wholly inside said housing;
  a plunger, axially moveable within the barrel;
  an inner housing intermediate the outer housing and the barrel and plunger; and
  an energy source in communication with said inner housing, wherein the inner housing is moveable by the energy source between three positions, namely
  a first position in which the inner housing is in communication with both the plunger and the barrel such that, in use, the plunger and barrel are movable axially so as to move at least part of said needle out of the outer housing;
  a second position in which the inner housing is in communication with the plunger but not the barrel such that, in use, said plunger is movable axially into said barrel so as to expel medicament through the needle; and
  a third position in which the inner housing is in communication with neither the plunger nor the barrel such that, in use, the plunger and barrel are able to retract in order to retract the needle into the outer housing.

The injection device according to the present invention provides a simple and cost-effective means of delivering medicament through a retractable needle. If desired, the device is able to deliver medicament to a depth beyond the length of the needle because of the propulsive force provided by the energy source. As mentioned above, the injection device is equally suitable for needle-assisted jet injection (delivering medicament to a depth beyond the length of the needle), conventional injection (to the depth of the needle penetration), or even to a user-adjustable needle penetration depth.

The device requires that the needle (and hence also the barrel to which it is normally fixed) is moved axially so that the needle can appear beyond the end of the nozzle for the duration of the injection, after which the needle retracts automatically, out of sight of the user. The device also requires that the plunger is moved axially (into the barrel) so that medicament is ejected. The overall complexity of the injection device is significantly reduced by both of these requirements being effected by one component, namely the inner housing.

Preferably, said inner housing includes one or more radially flexible tags, each preferably located at the end of a resiliently flexible leg.

Preferably, one or more of said tags are situated at the rear end of the inner housing and are moveable radially into and out of communication with the plunger. In one embodiment, the tags are biased radially inwardly into communication with the plunger, preferably by communication with the outer housing. Alternatively, the tags are stored in their relaxed condition, before an injection is initiated.

Each rear tag may be moveable out of communication with the plunger when aligned with a corresponding recess in the outer housing. Preferably, each rear tag is substantially T-shaped. One leg of the T-shape enables the rear tag to hook over the plunger and, effectively, pull the plunger forward (in the first and second positions mentioned above). The other leg of the T-shape enables the rear tag to move radially outwardly to catch in a recess in the housing (in the third position mentioned above).

Preferably, one or more of said tags are situated at the forward end of the inner housing and are moveable radially into and out of communication with the barrel. In one embodiment, the forward tags are biased radially inwardly into communication with the barrel, preferably by communication with the outer housing. Alternatively, the forward tags are stored in their relaxed condition, before initiating an injection.

Each forward tag may be moveable out of communication with the barrel when aligned with a corresponding recess in the outer housing. Preferably, each rear tag is substantially L-shaped.

In a preferred embodiment, said energy source is a compressed gas. Alternatively, said energy source is a spring.

Preferably, the injection device further includes means for allowing the inner housing to move axially only forward with respect to the outer housing. Ideally, said means is an arrangement of serrations, barbs, ratchet teeth or the like intermediate the housings.

Preferably, the injection device further comprises guide means for guiding, in use, the relative axial movement of the inner and outer housings, the guide means preferably comprising one or more protrusions on said inner housing which, in use, cooperate with corresponding recesses on an interior surface of said outer housing.

Preferably, said needle is biased to be normally wholly inside said housing by means of a spring intermediate the barrel and the outer housing.

In one embodiment, the needle is removable from the device, this being of benefit in applications where the device is reusable (for example if a multiple-use cartridge of medicament is utilised).

In a further embodiment, said needle, barrel and plunger are removable from said device. It is intended that the device of the present invention could be constructed around a standard needle, barrel and plunger of known type.

Preferably, the injection device further includes a removable needle cover which protects the needle during storage and before use. Advantageously, said needle cover includes means for pulling a protective rubber sheath or the like from said needle when said needle cover is removed from the device. Said pulling means may include a floating rivet intermediate the needle cover and the protective rubber sheath or the like, whereby twisting forces applied to said needle cover are substantially prevented from being transmitted to said rubber sheath or the like.

Preferably, the presence of said needle cover on said device serves as a safety lock, substantially preventing relative forward movement of said outer housing.

In a preferred form, the injection device further comprises a viewing window in said barrel aligned with a viewing window in said outer housing such that said medicament can be viewed by a user prior to an injection taking place. Preferably, in use during an injection, said inner housing moves intermediate said viewing window in the outer housing and said barrel so as to obscure the window in the barrel from the user's view.

Preferably, the injection device includes means for emitting an audible and/or physical indication to a user that the injection is complete.

According to a second aspect of the invention there is provided an injection device comprising an outer housing inside which is located a barrel for holding a volume of a medicament;
a needle at one end of the barrel, the needle and barrel being such that at least part of the needle is axially moveable in and out of said outer housing but is biased to be normally wholly inside said housing;
a plunger, axially moveable within the barrel;
an inner housing intermediate the outer housing and the barrel and plunger; and
an energy source in communication with said inner housing, wherein the inner housing is moveable by the energy source between two positions, namely
a first position in which the inner housing is in communication with the plunger but not the barrel such that, in use, said plunger is movable axially into said barrel so as to expel medicament through the needle; and
a second position in which the inner housing is in communication with neither the plunger nor the barrel such that, in use, the plunger and barrel are able to retract in order to retract the needle into the outer housing.

According to a third aspect of the invention there is provided an injection device comprising an outer housing adapted to receive:

a barrel for holding a volume of a medicament;
a needle at one end of the barrel, the needle and barrel being such that at least part of the needle is axially moveable in and out of said outer housing but is biased to be normally wholly inside said housing; and
a plunger, axially moveable within the barrel, characterised in that the injection device further comprises:
an inner housing intermediate the outer housing and the barrel and plunger; and
an energy source in communication with said inner housing, wherein the inner housing is moveable by the energy source between three positions, namely
a first position in which the inner housing is in communication with both the plunger and the barrel such that, in use, the plunger and barrel are movable axially so as to move at least part of said needle out of the outer housing;
a second position in which the inner housing is in communication with the plunger but not the barrel such that, in use, said plunger is movable axially into said barrel so as to expel medicament through the needle; and
a third position in which the inner housing is in communication with neither the plunger nor the barrel such that, in use, the plunger and barrel are able to retract in order to retract the needle into the outer housing.

Preferred embodiments of the present invention will now be more particularly described, by way of example only, with reference to the accompanying drawings wherein:

FIG. 1 is a perspective view, partly in section, showing the injection device, in the condition in which it is supplied to a user, apart from the needle cover;

FIG. 2, drawn to a larger scale, shows detail of part of the device shown in FIG. 1;

FIG. 3 is a perspective view, partly in section, showing the injection device, during an injection;

FIG. 4, drawn to a larger scale, shows detail of part of the device shown in FIG. 3;

FIG. 5 is a perspective view, partly in section, showing the injection device, with the plunger fully depressed into the barrel;

FIG. 6, drawn to a larger scale, shows detail of part of the device shown in FIG. 5;

FIG. 7 is a perspective view, partly in section, showing the injection device, after use and safe to dispose of;

FIG. 8, drawn to a larger scale, shows detail of part of the device shown in FIG. 7;

Figure 15:
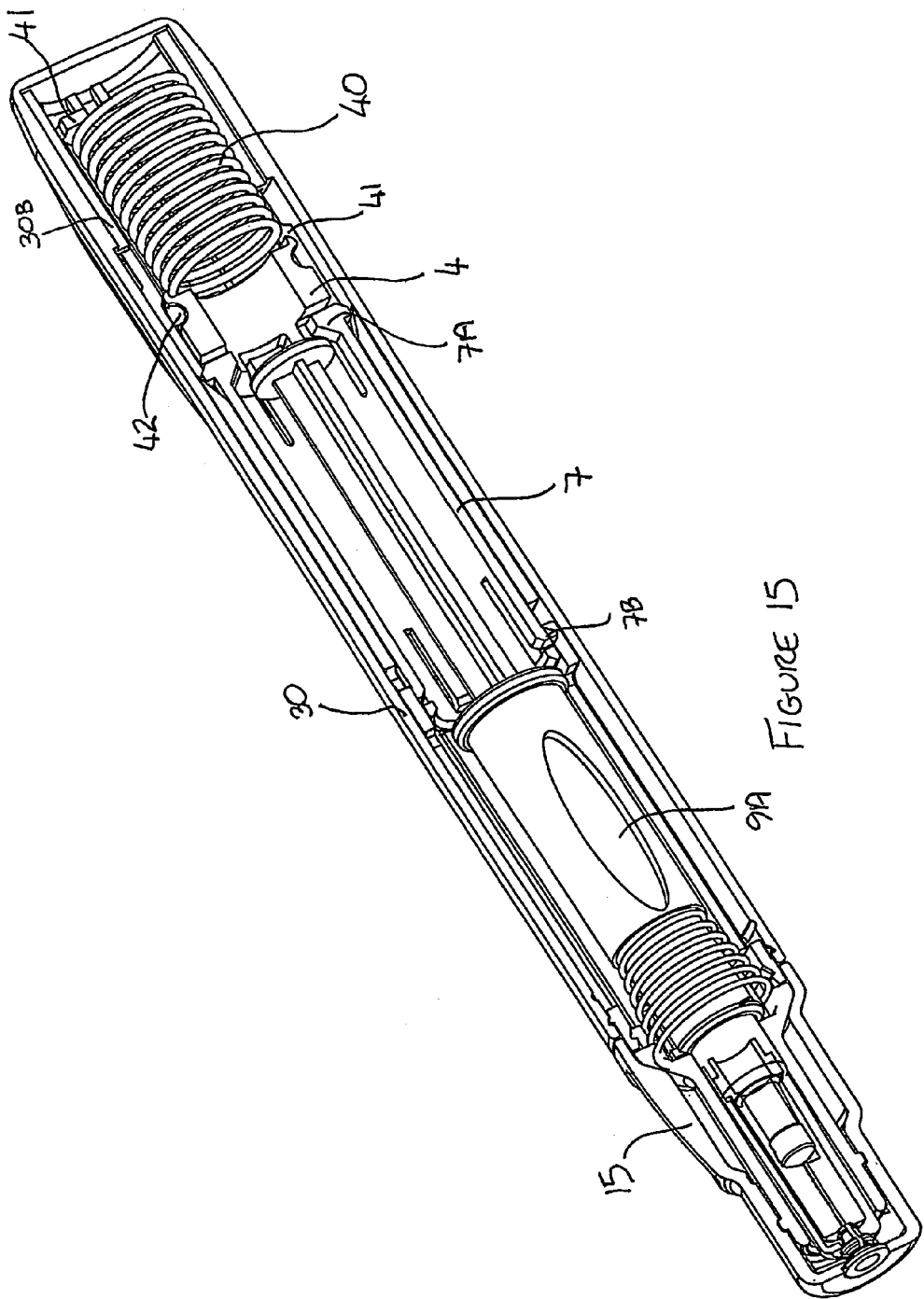
FIG. 15 is a perspective view, partly in section, showing an alternative embodiment of the injection device, in the condition in which it is supplied to a user.
Figure 16:
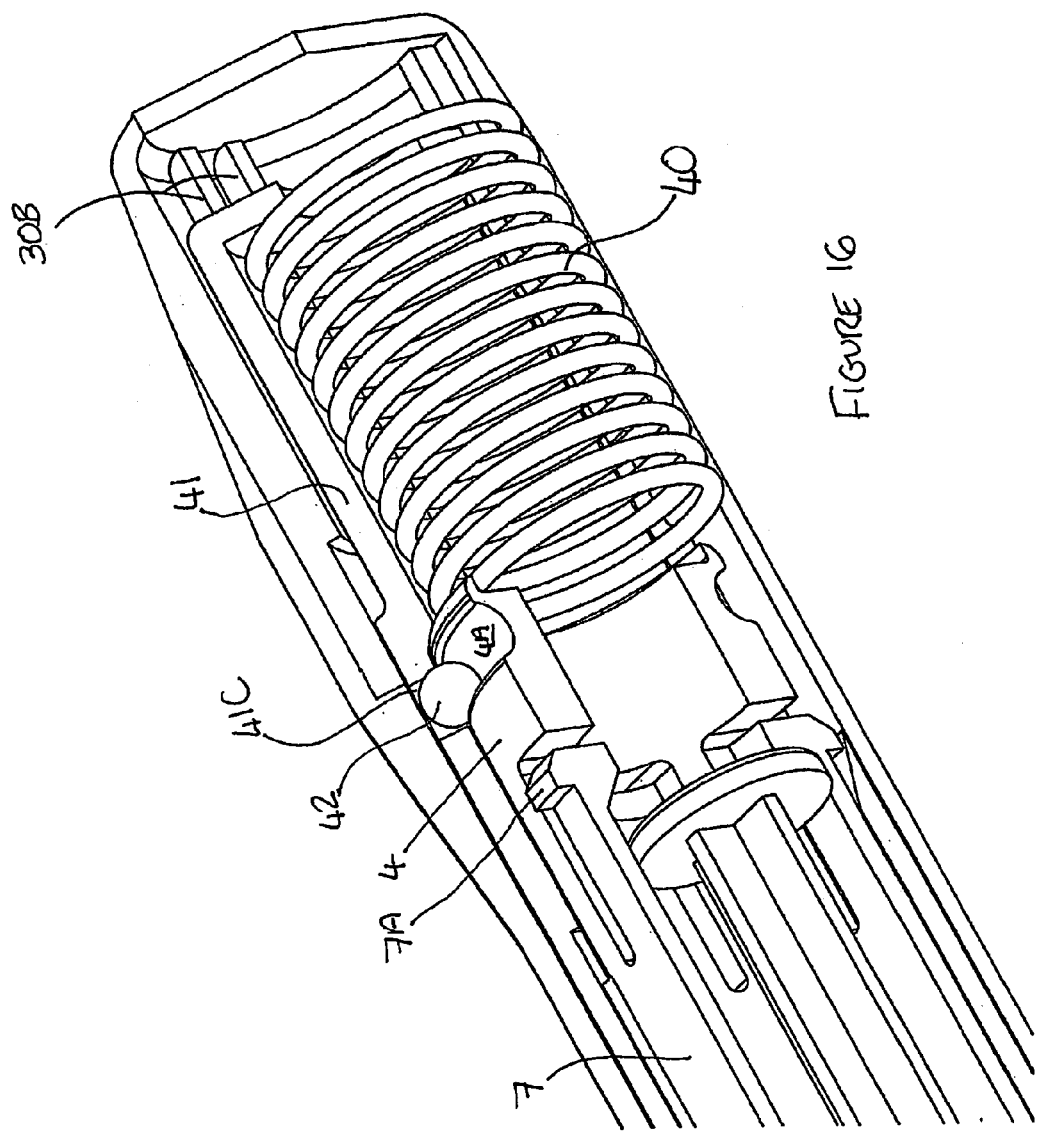
Figure 17:
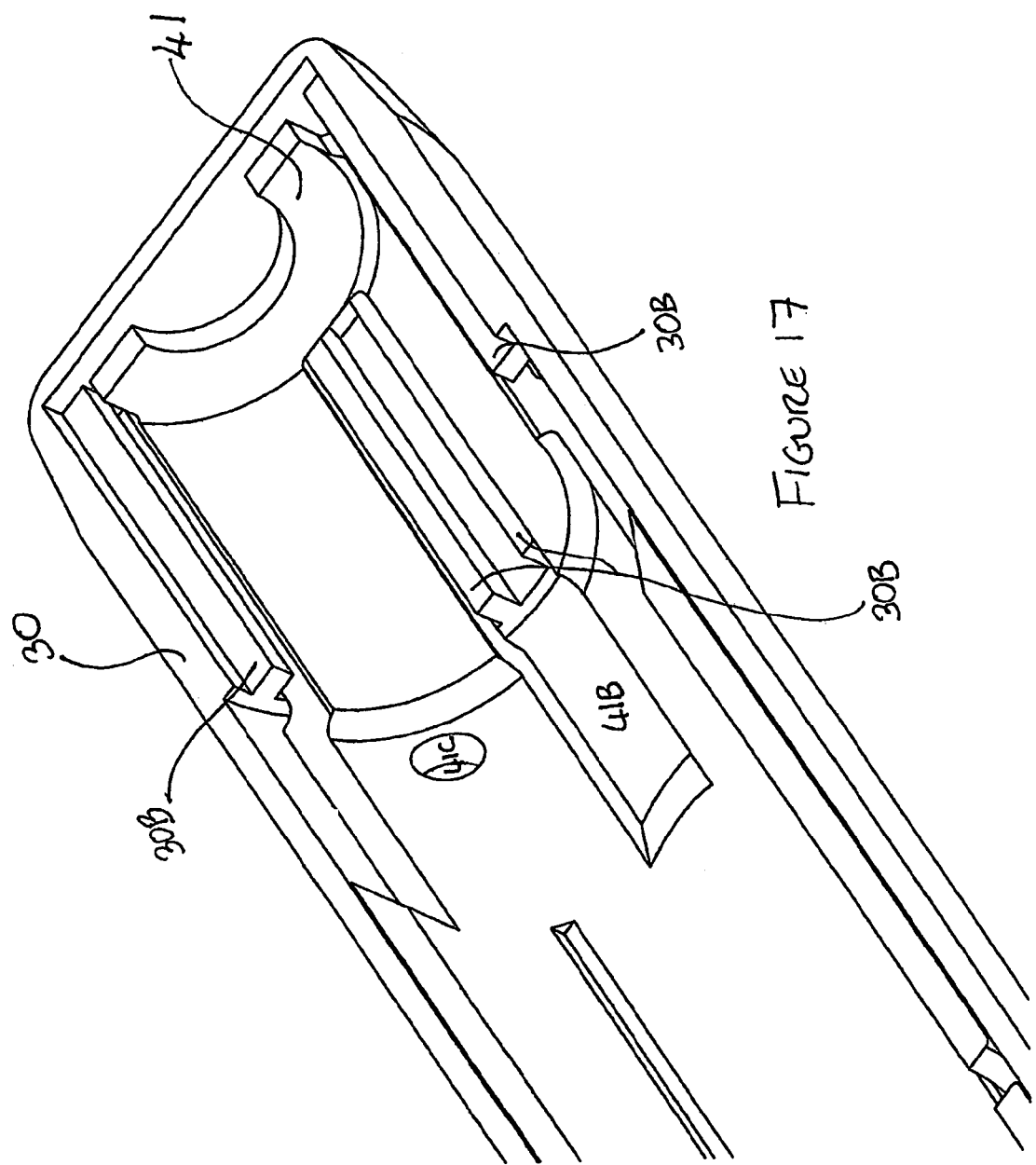
Figure 18:
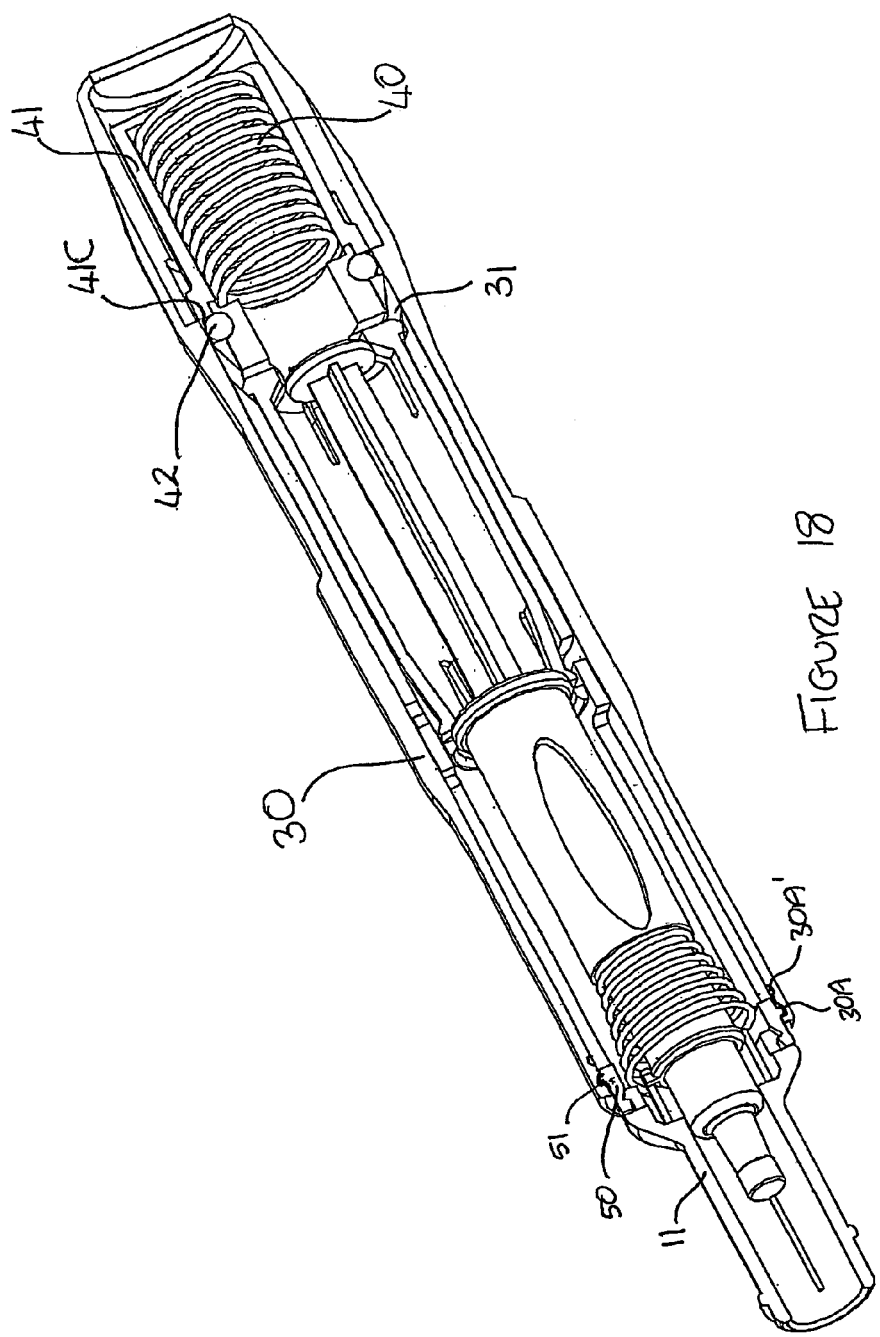
Figure 19:
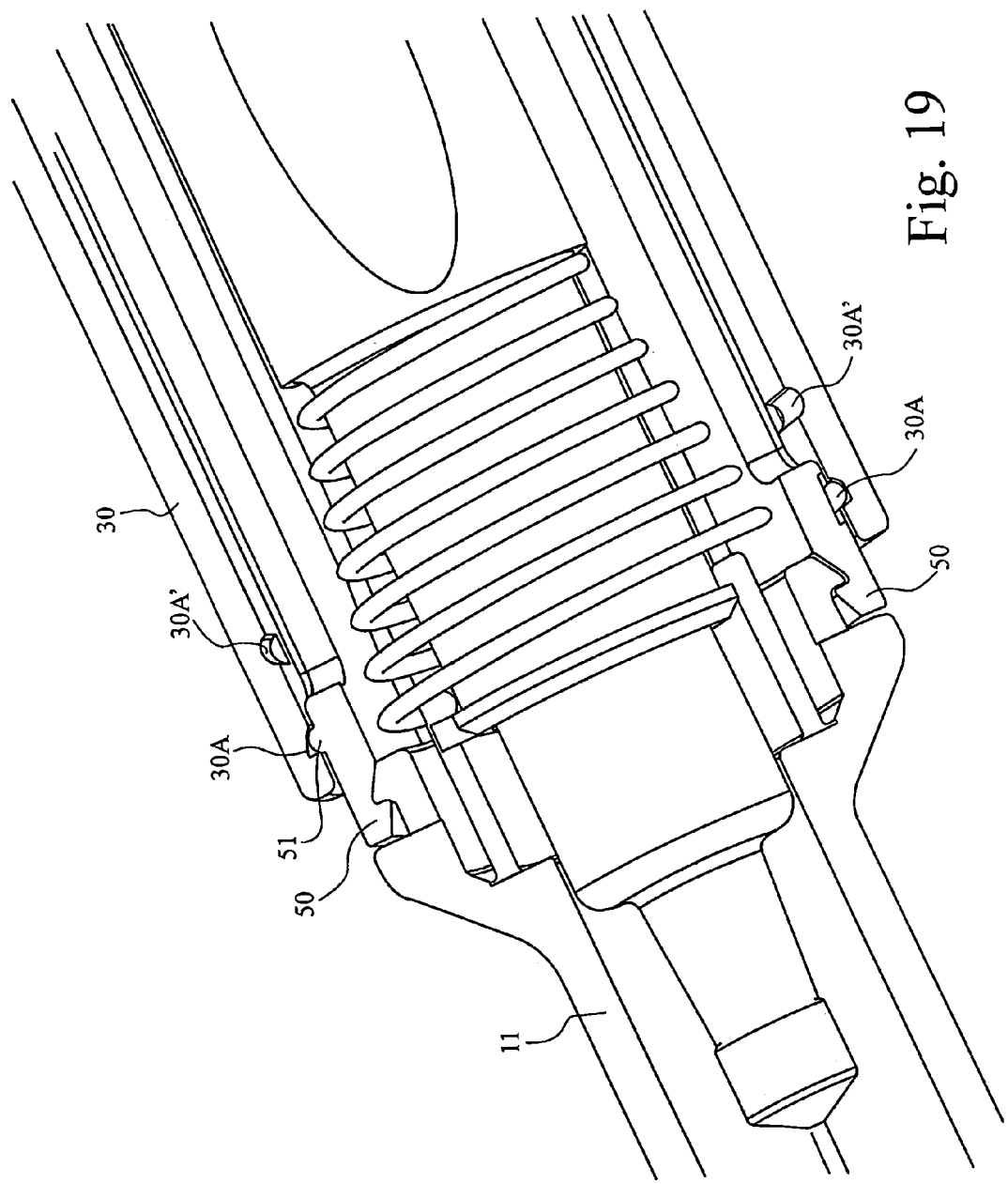
Figure 20:
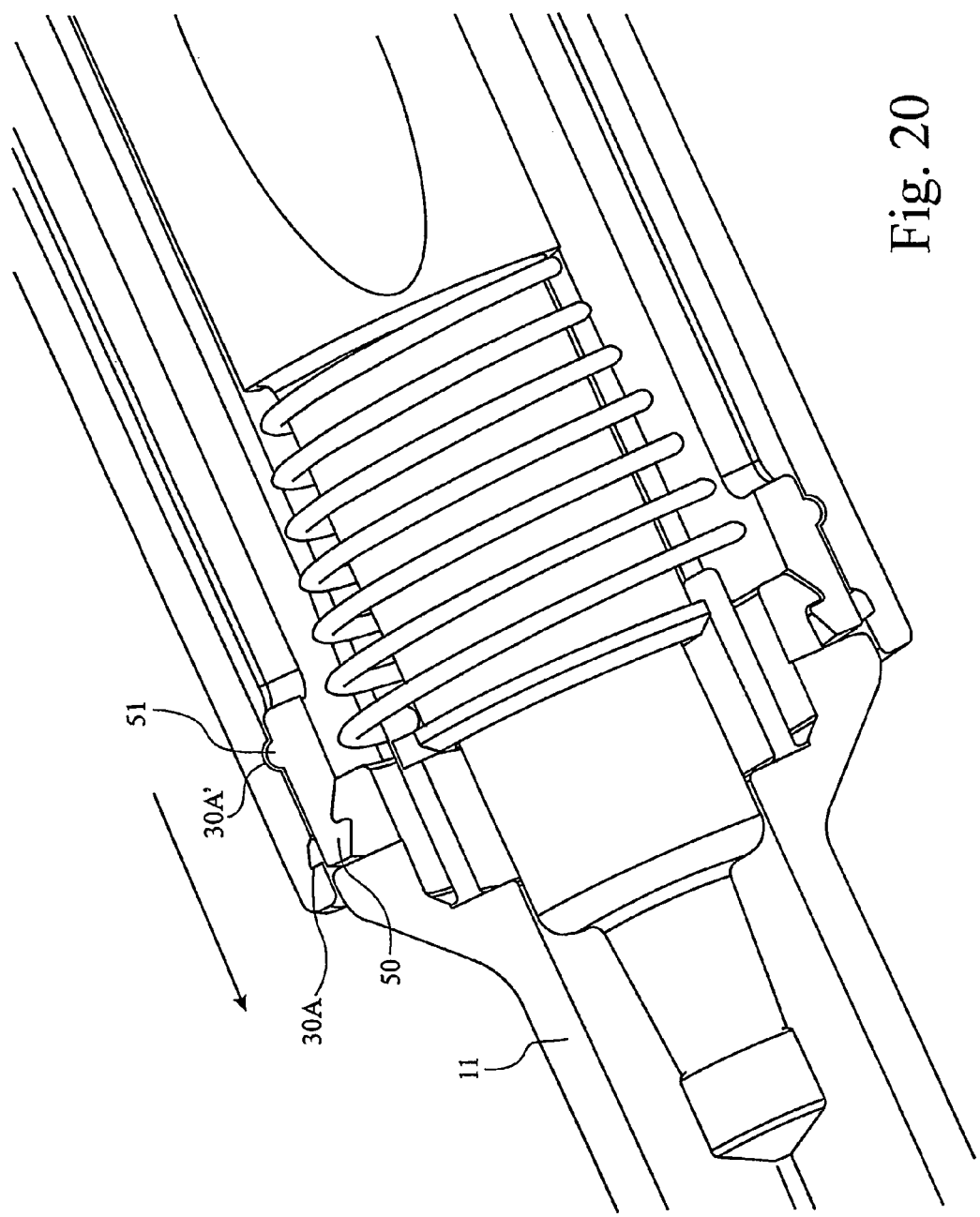
Figure 21:
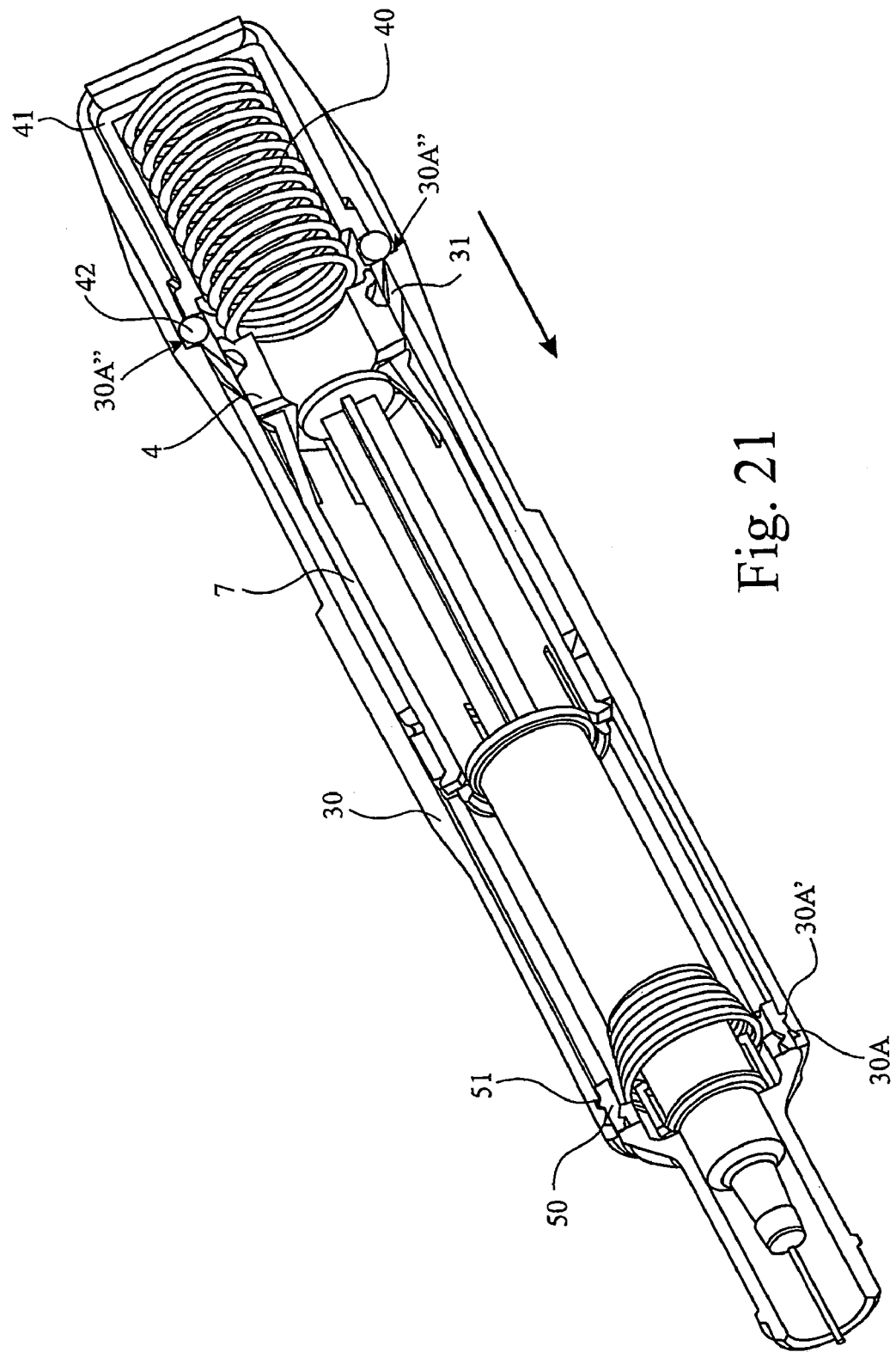
Figure 22:
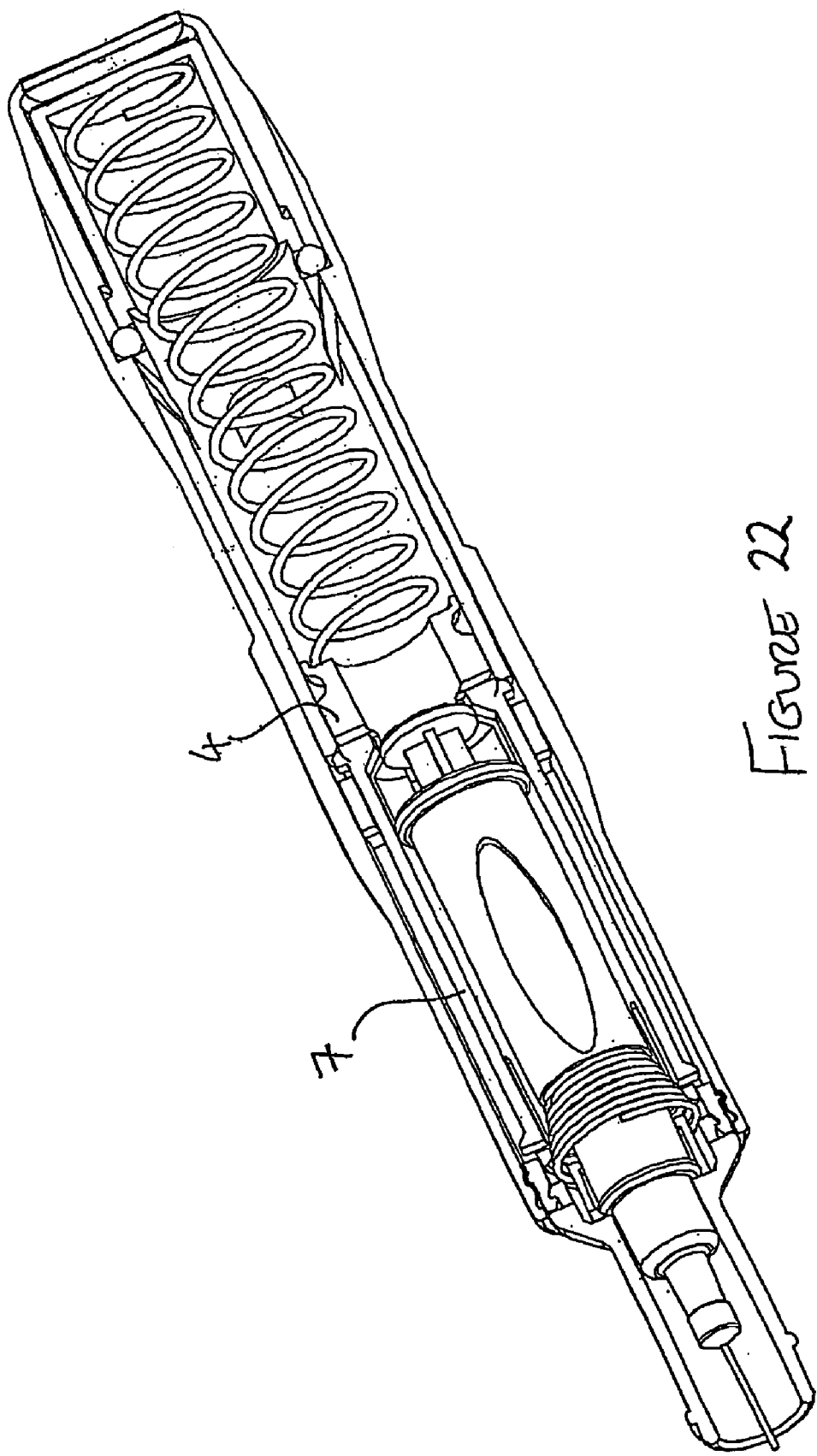
Figure 23:
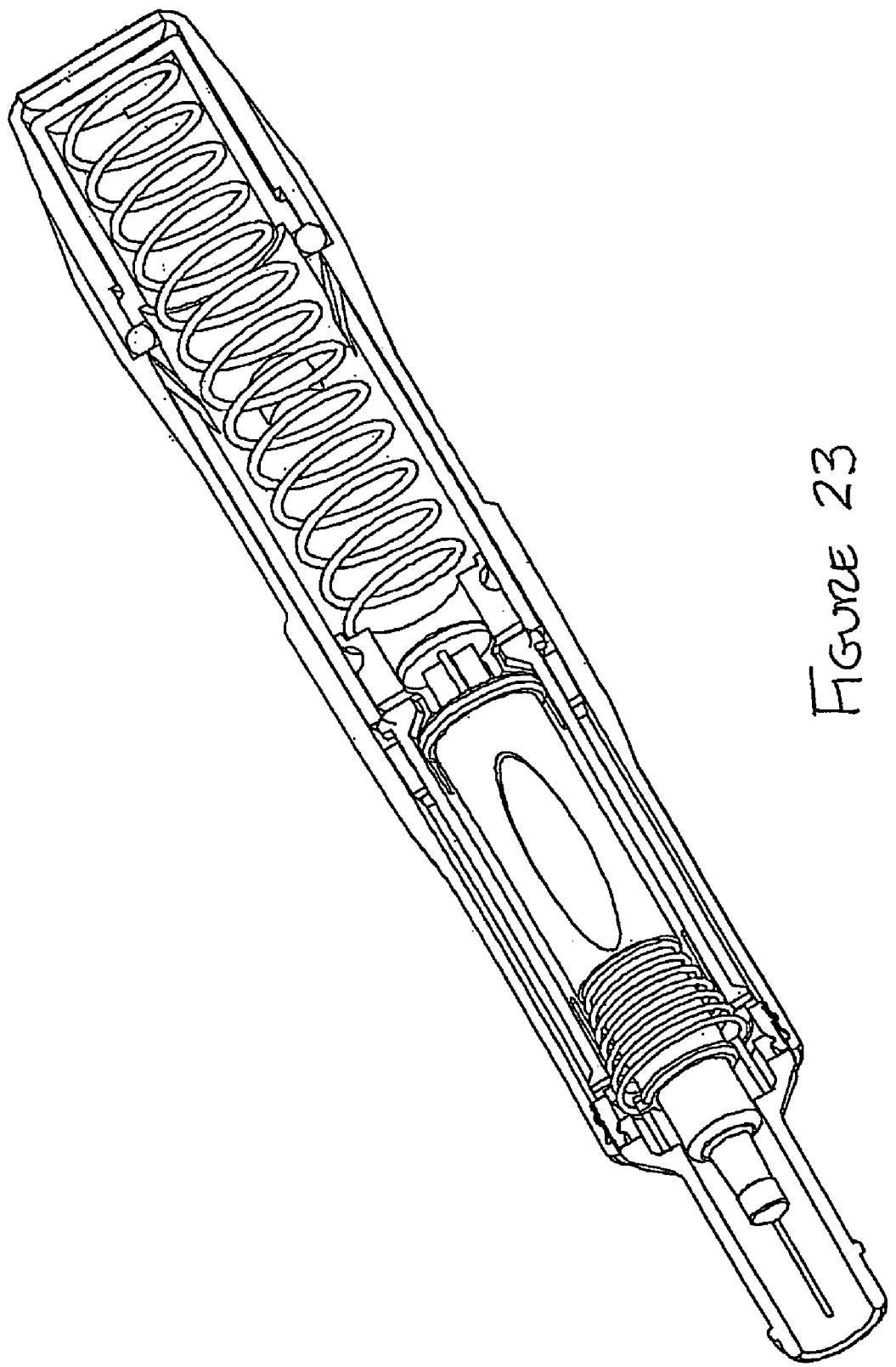
Figure 24:
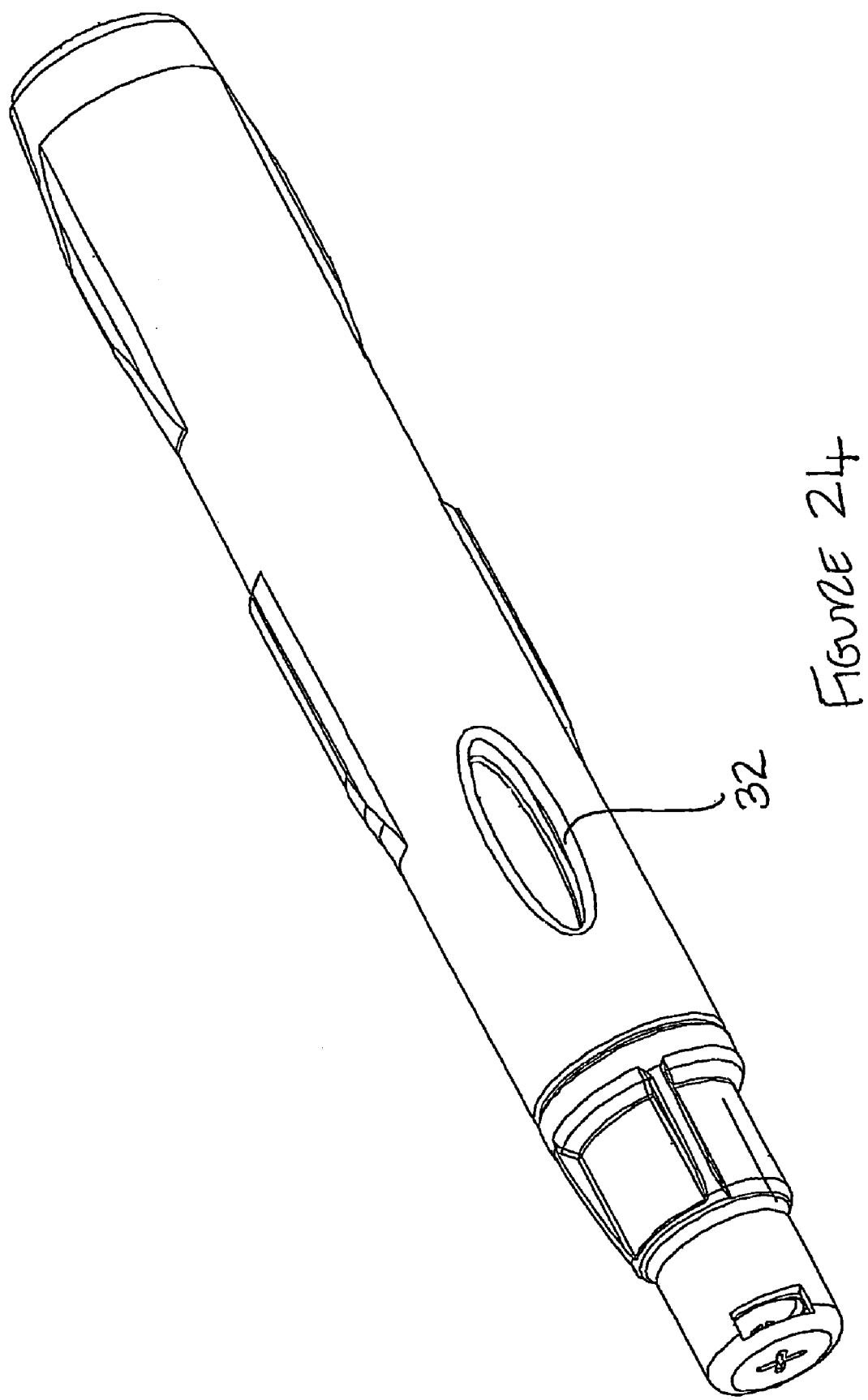
Figure 25:
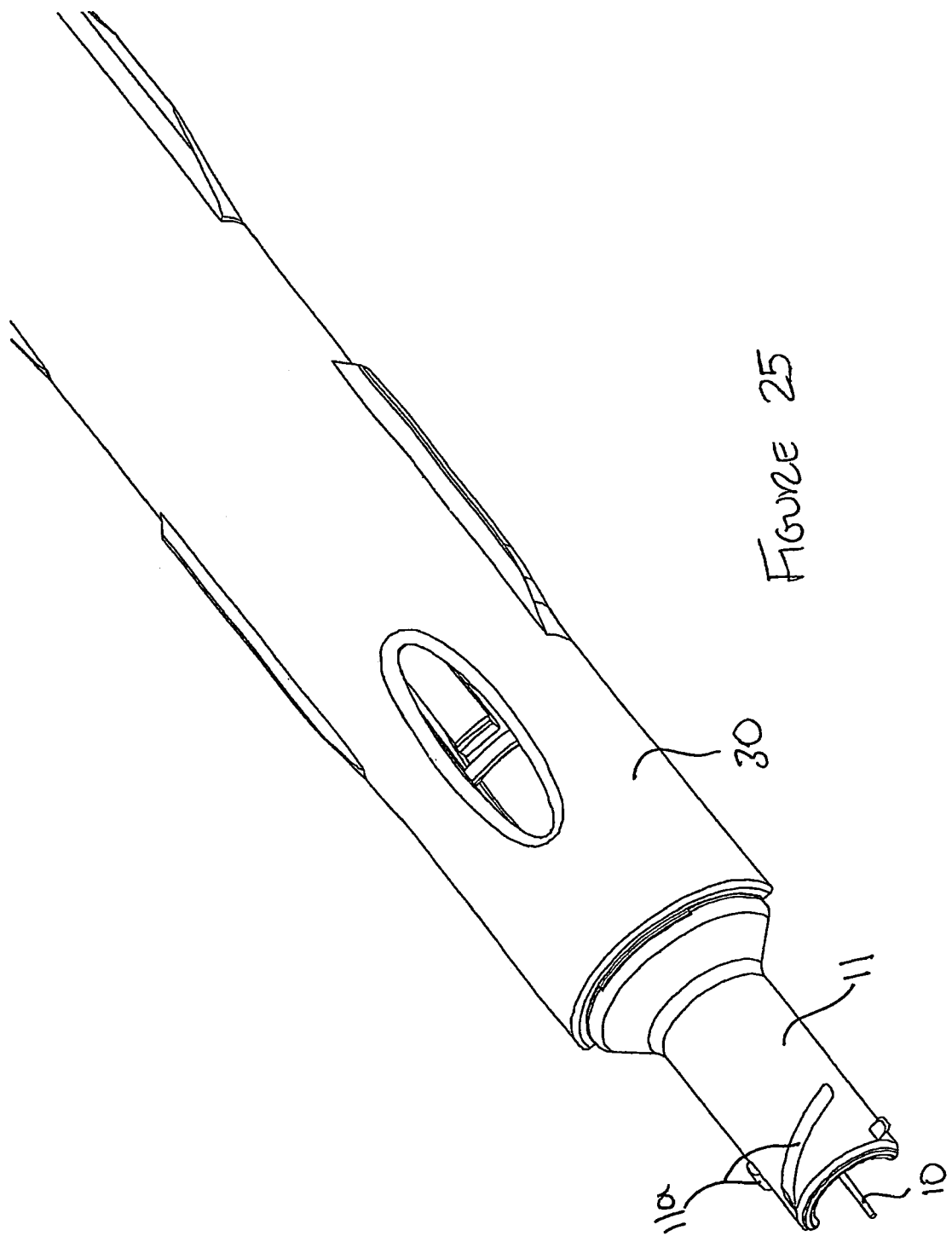

FIG. 16, drawn to a larger scale, shows detail of the rear end of the device shown in FIG. 15;

FIG. 17 shows detail of the interaction between the spring housing 41 and the rear of the outer housing 30;

FIG. 18 is a perspective view, partly in section, showing the injection device with the needle cover removed, immediately prior to initiating an injection;

FIG. 19 is a perspective view, partly in section and drawn to a larger scale, showing the front part of the device immediately before initiating an injection;

FIG. 20 is a perspective view, partly in section, showing the front part of the device at the start of an injection;

FIG. 21 is a perspective view showing the device in the same condition as FIG. 20, i.e. at the start of an injection with the needle emerging from the end of the device and the plunger beginning to travel down the barrel;

FIG. 22 is a perspective view, partly in section, showing the injection device with the plunger fully depressed into the barrel;

FIG. 23 is a perspective view, partly in section, showing the injection device after use and with the needle retracted into the device;

FIG. 24 is a perspective view of the assembled device, including the needle cover;

FIG. 25 is a schematic view of part of the front end of the device, showing the helical protrusion on the nozzle.

Figure 26:
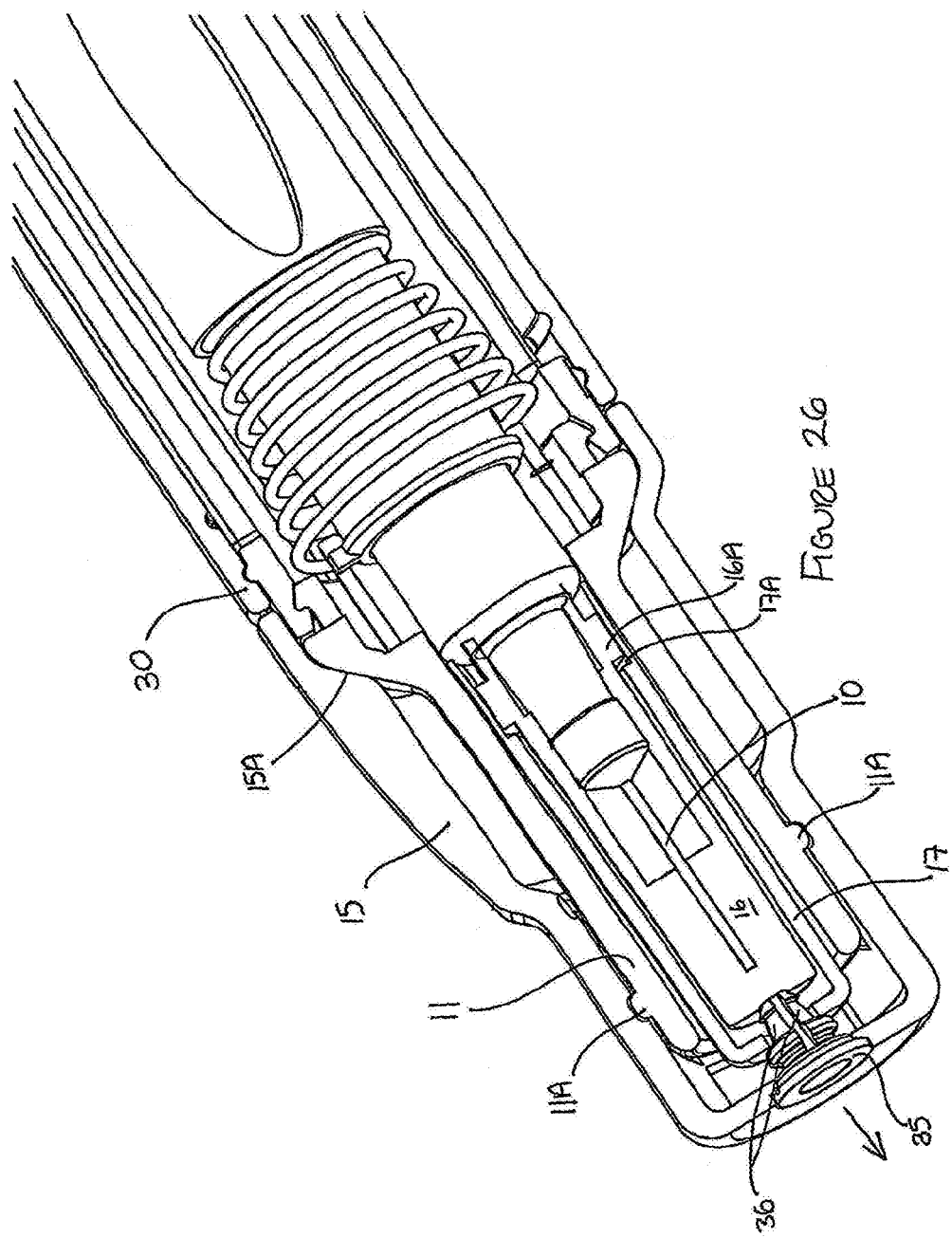
Figure 27:
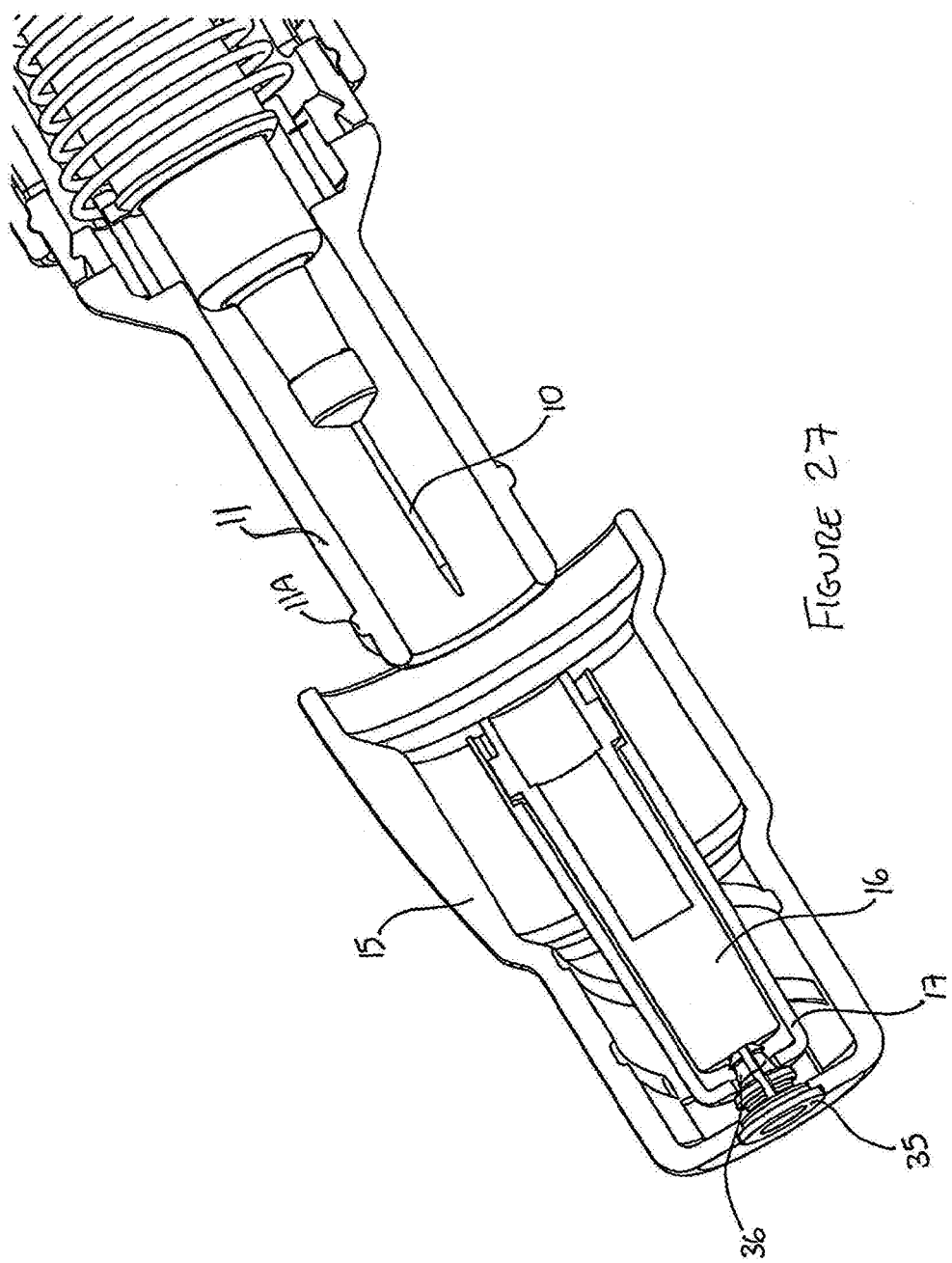

FIG. 26 is perspective view, partly in section, showing detail of the needle cover; and FIG. 27 is perspective view, partly in section, showing detail of the needle cover after removal from the device.

Throughout the following description, reference to a "forward" direction means the direction which is towards the patient when the injection device is in use. The "forward" end of the injection device is the end nearest the patient's skin when the device is in use. Similarly, reference to a "rearward" direction means the direction which is away from the patient and the "rearward" end of the device is the end furthest from the patient's skin when the injection device is in use.

Figure 1:
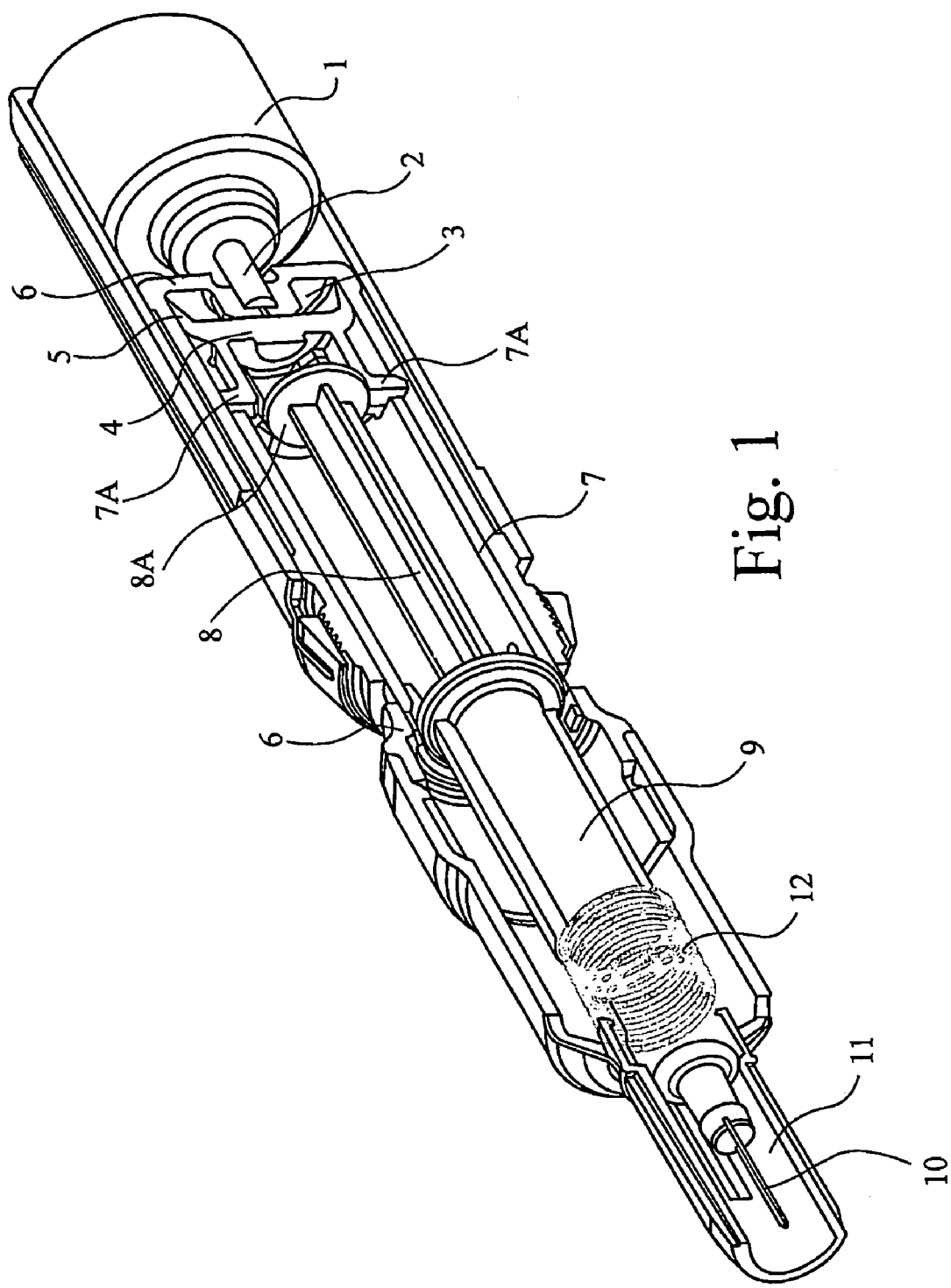

FIG. 1 is a perspective view, partly in section, showing the injection device, in the condition in which it is supplied to a user, apart from the needle cover (which is described below after describing the main operation of the device).

The principal components of the device will now be described with reference to FIGS. 1 and 2. An energy source 1 is provided at the rear of the device which, in this embodiment, is a gas cylinder similar to the type used in a conventional aerosol can or the like i.e. having a valve through which gas can be released at will and in a controlled manner. In an alternative embodiment of the invention, a spring is used as the energy source in place of a gas cylinder and this embodiment is described later with reference to FIG. 13 et seq.

The valve 2 of the gas cylinder opens into a chamber 3, which in FIG. 1 is of relatively small volume. The front wall of the chamber 3 is defined by a ram 4 which has an annular seal 5 at the rear thereof in order to make the chamber 3 gas-tight. The rear wall of the chamber 3 is defined by the back face of a generally cylindrical chamber housing 6.

Figure 13:
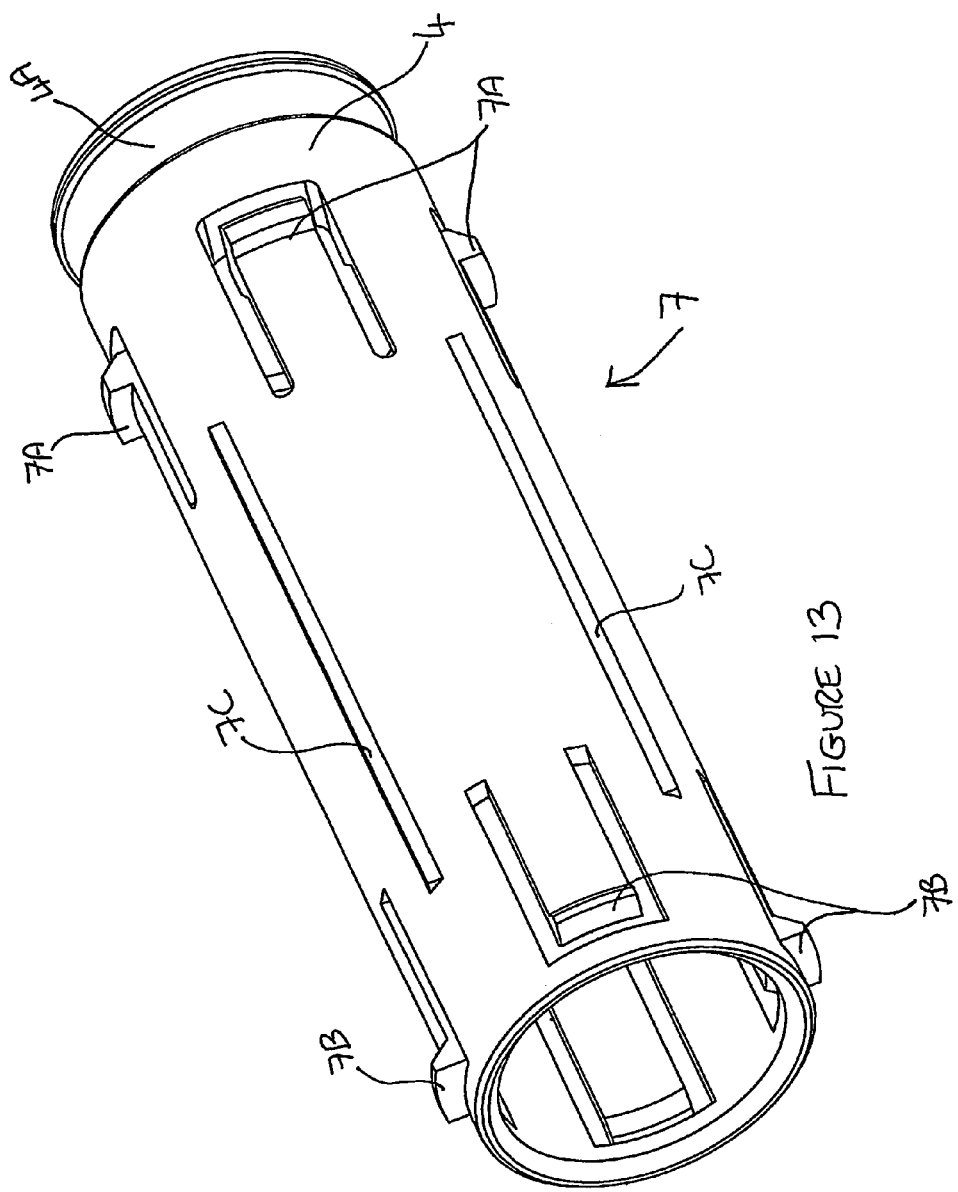
FIG. 13 is a perspective view of the inner housing (also referred to as the "plunger housing")
Figure 14:
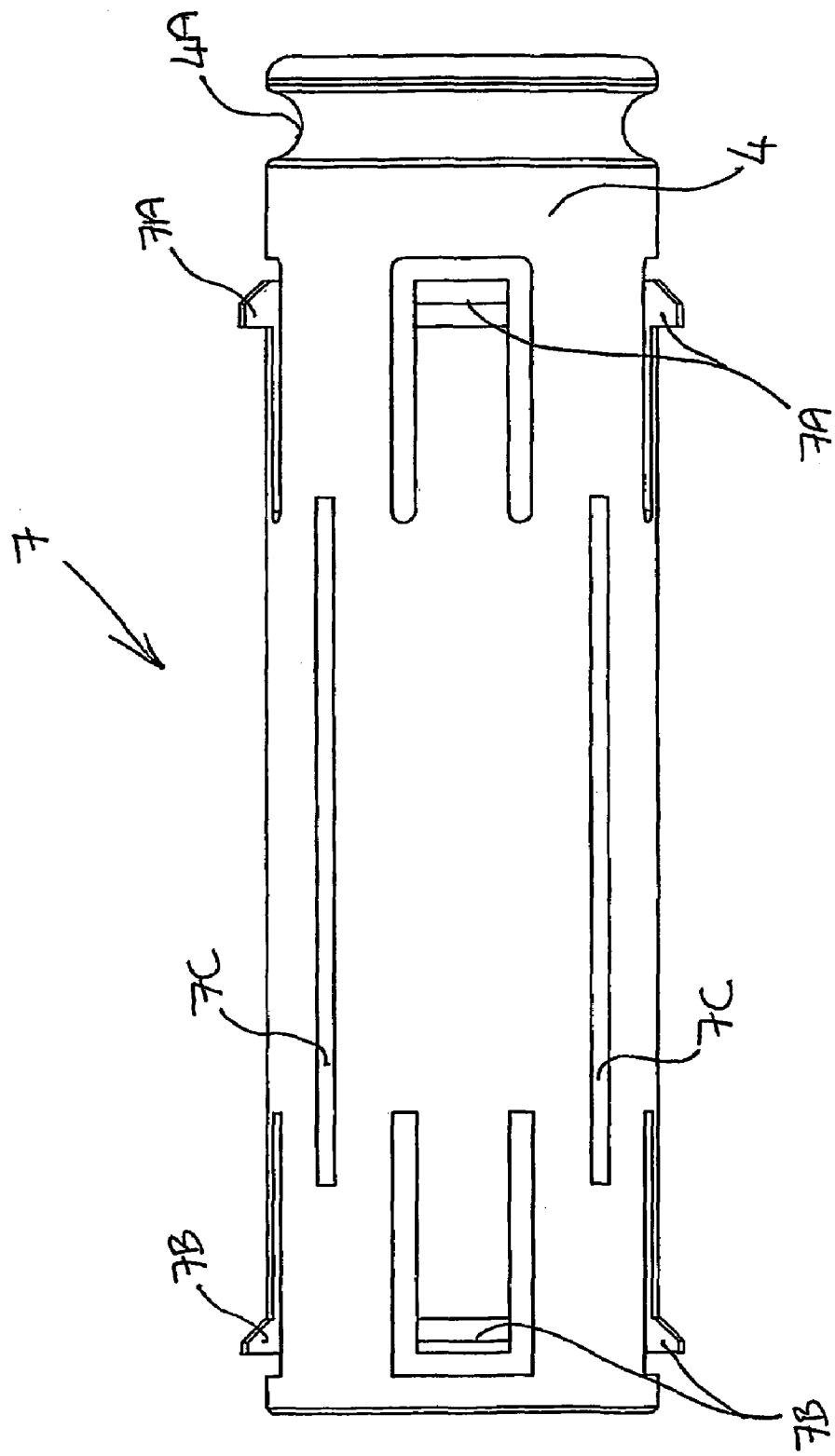
FIG. 14 is a side view of the inner housing of FIG. 13.

The forward part of the ram 4 abuts or alternatively is integrally-formed with an inner housing 7 which closely surrounds a plunger 8 (and can therefore be referred to as the "plunger housing"). The rear of the plunger housing includes four orthogonally placed tags 7A, which each have a "hammer head" or T-shape and whose tendency to spring radially outwardly is restricted by the diameter of the chamber housing 6. If the ram 4 is integrally formed with the plunger housing 7 as illustrated in FIGS. 13 and 14, the tags 7A are positioned at the end of flexible legs cut into the housing, so that the tags 7A can move radially, with respect to the ram 4 and remainder of housing 7.

Figure 2:
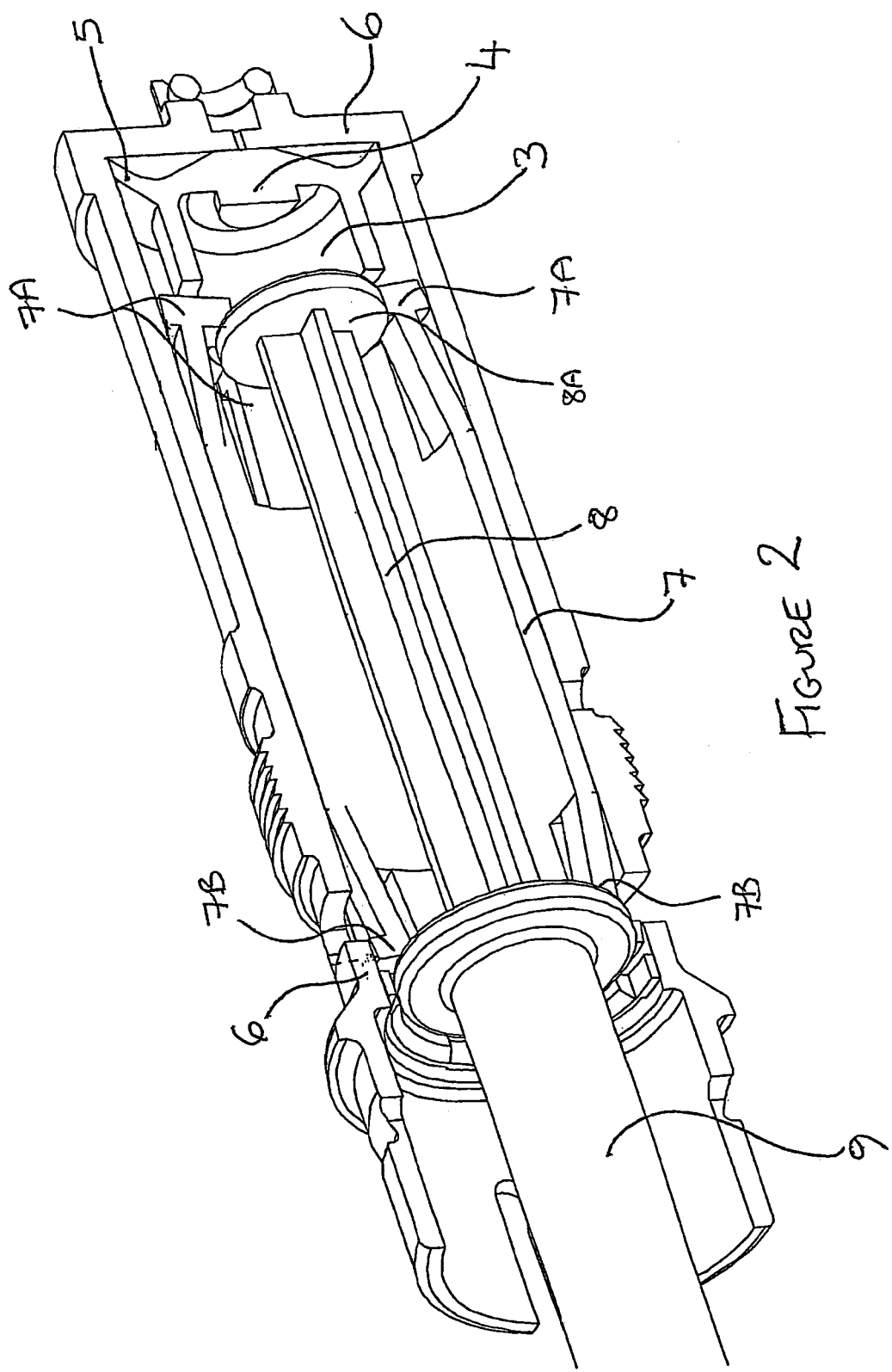

The hammer head of each tag 7A hooks over the enlarged head 8A of the plunger 8, so that the tags 7A are in contact with the plunger head 8A, as shown best in FIG. 2.

The plunger 8 is the plunger of a syringe arrangement comprising a barrel 9 in which a predefined volume of liquid medicament is supplied and a needle 10 through which the medicament can be delivered to the patient. A nozzle 11 at the front end of the injection device normally conceals the needle 10 from the user's view. A spring 12, positioned between the outer housing and the barrel 9 biases the needle to be normally wholly within the nozzle 11.

At the front end of the plunger housing 7, there are further orthogonally placed tags 7B, which each have a generally L shape and whose tendency to spring radially outwardly is restricted by the diameter of the chamber housing 6. The tags 7B each abut the flange at the rear of barrel 9.

Other means of interaction between the inner housing and the plunger may be envisaged, instead of tags 7A, for example tags that are not T-shaped, or means that push the plunger rather than pulling as in the described embodiment.

There are four main stages in the operation of the device. Stage 1 is the condition shown in FIGS. 1 and 2, i.e. the device as supplied to a user, and as described above. The medicament is already present in the barrel 9 and the needle 10 is concealed from view within the nozzle 11. The plunger 8 is fully withdrawn from the barrel 9 (because of the liquid medicament contained within the barrel) and the head of the plunger 8A abuts the tags 7A. The rear of the remainder of housing 7 abuts the ram 4. The chamber 3 is of minimal volume.

Figure 3:
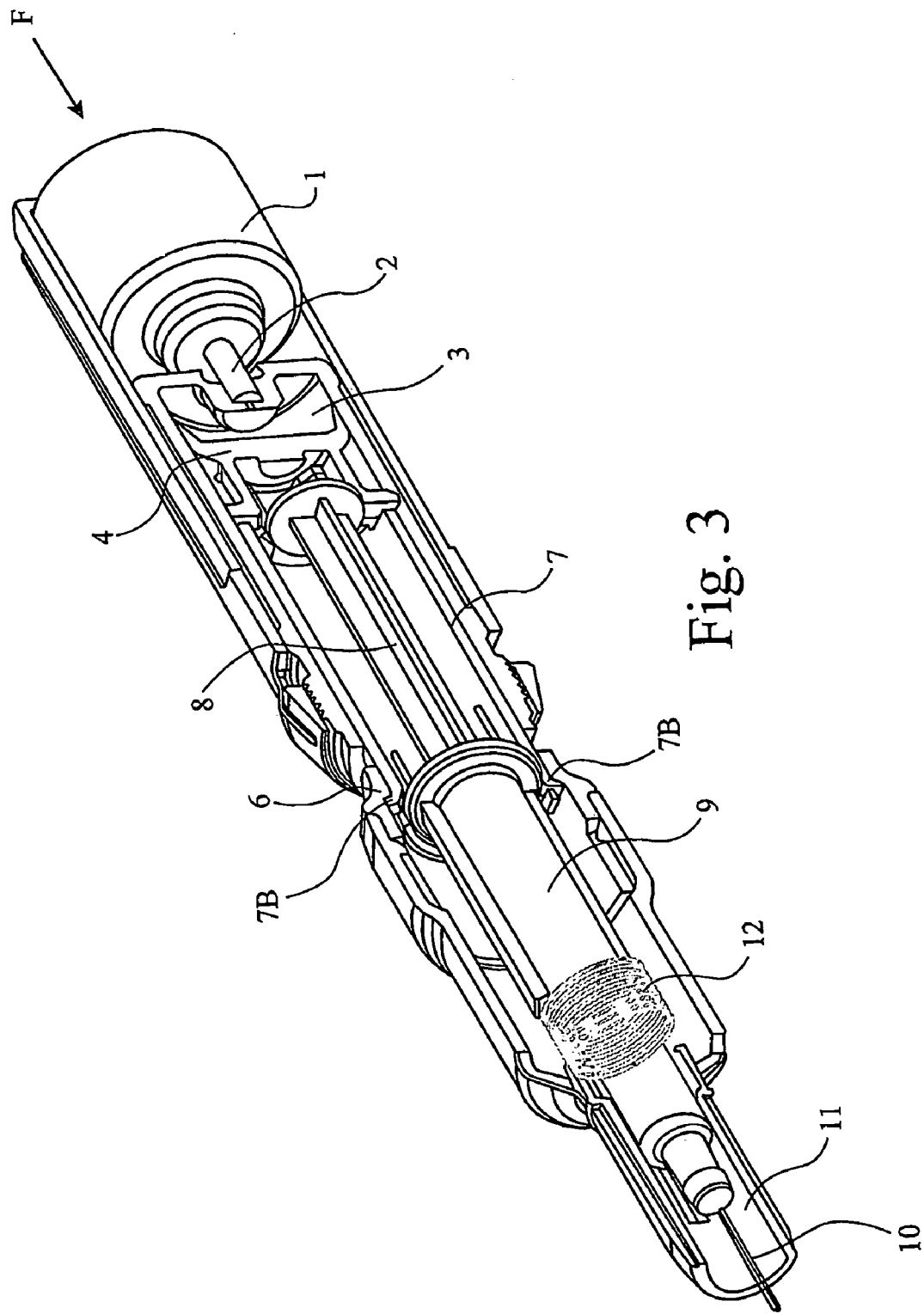
Figure 4:
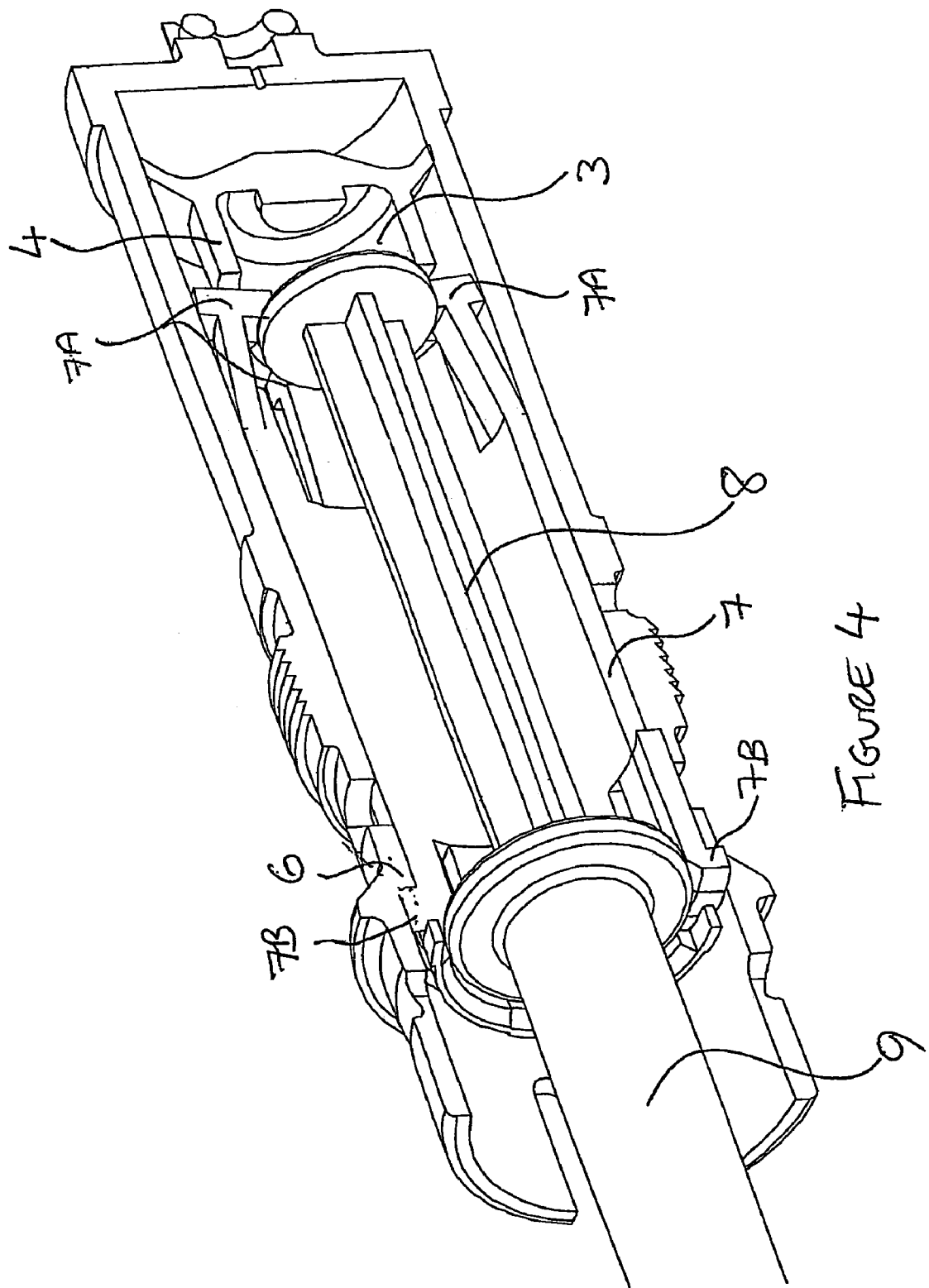

Stage 2 of operation is the injection stage illustrated in FIGS. 3 and 4. With the injection device held against the patient's skin at the injection site, downward force is applied to the device in the direction indicated by the arrow F in FIG. 2. This force causes the valve of the gas cylinder 1 to open, releasing gas into the chamber 3. As the chamber 3 fills with gas, the ram 4 is urged forward, consequently urging tags 7A against the plunger 8. As the tags 7A, and hence the plunger housing 7, are urged forward, the cooperation of the tags 7B against the barrel 9 means that the barrel is also urged forward, against the bias of a spring 12 (shown in FIG. 3). As the barrel 9 moves forward, so does the needle 10 which is attached thereto and so the needle protrudes out of the nozzle 11 sufficiently to enable an injection to be delivered. Therefore, initially, the ram 4 causes the plunger housing 7, the plunger 8, the barrel 9 and the needle 10 to move forwards.

Shortly after the plunger housing 7 starts to move forward, the tags 7B reach a lip in the chamber housing 6. The tags 7B spring radially outwardly over this lip, as shown in FIGS. 3 and 4. Once the tags 7B have sprung outwardly in this way, they are no longer in abutment with the barrel 9. This means that the barrel 9 (and hence needle 10) is no longer urged forwards because the forwardly-moving plunger housing 7, including tags 7B, are free to continue moving forward without contacting the barrel 9.

Therefore, once the device has reached the condition illustrated in FIGS. 3 and 4, continued forward movement of the ram 4 and plunger housing 7 causes the plunger 8 to be urged forward into the barrel 9. This expels the liquid medicament from the barrel 9, through the needle 10 to deliver an injection. It is the cooperation of the tags 7A with the enlarged head 8A of the plunger which transmits the forward force from the ram 4/housing 7 to the plunger 8.

Figure 5:
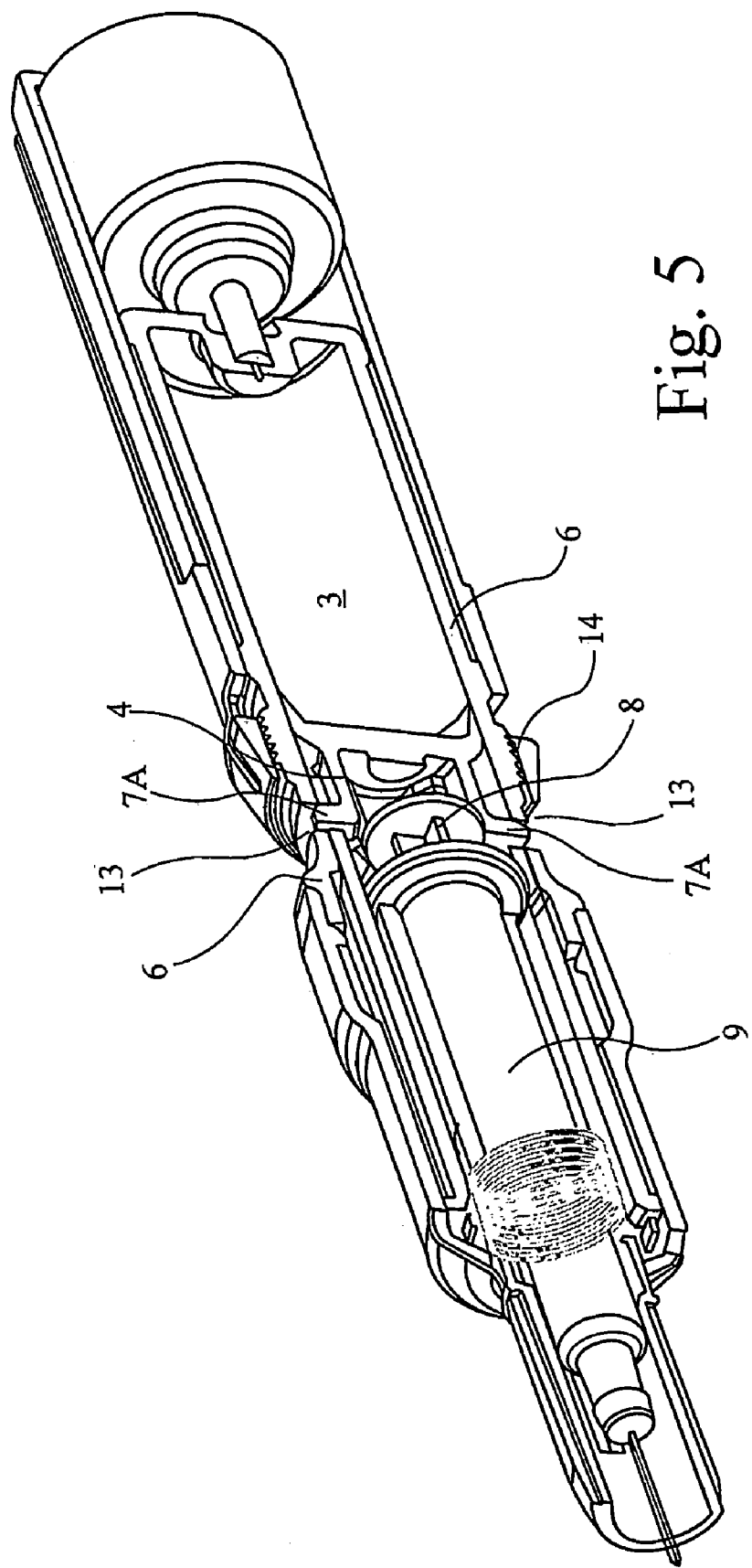
Figure 6:
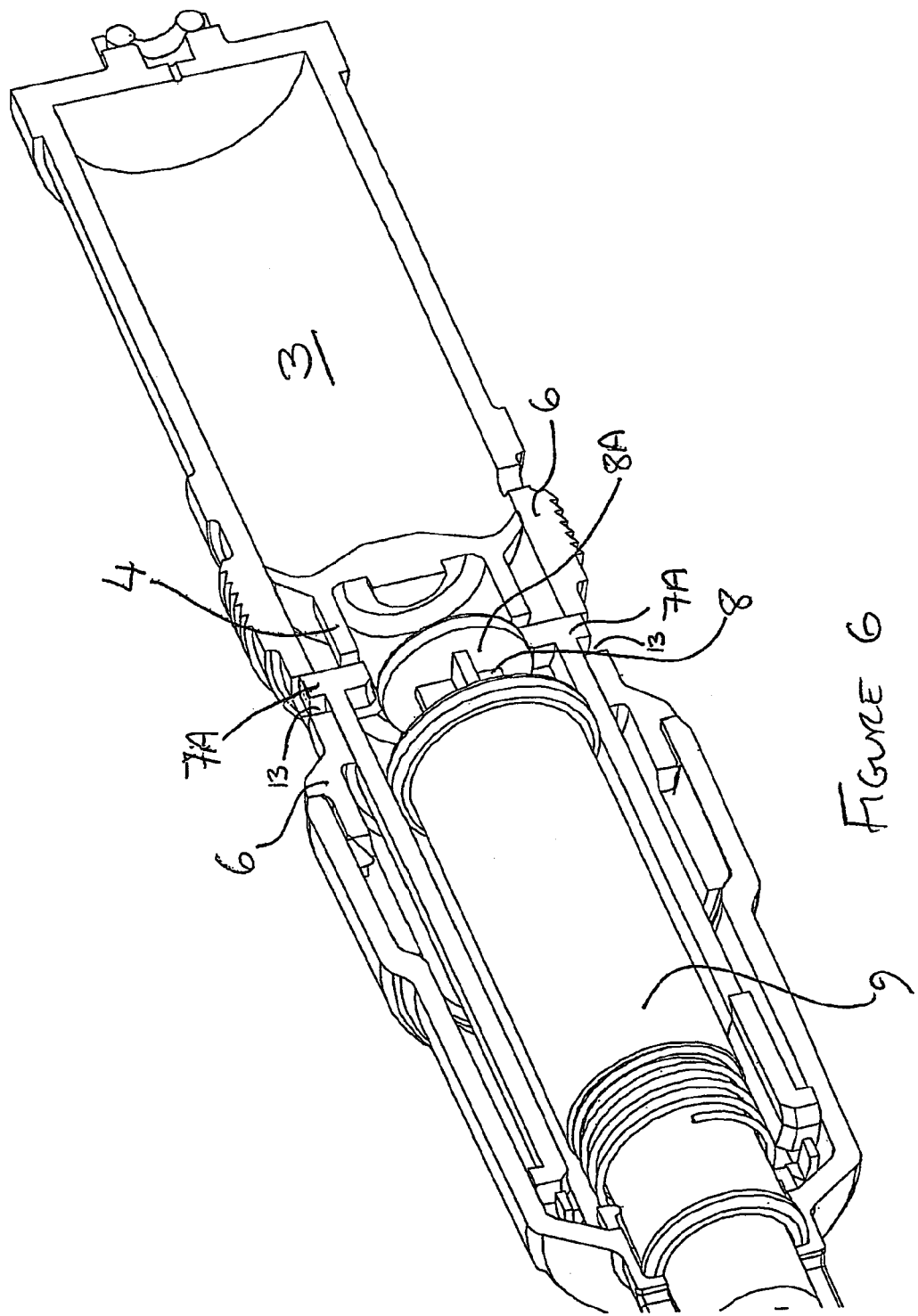

The third stage in the operation of the device is illustrated in FIGS. 5 and 6. When the plunger 8 is depressed into the barrel 9, the desired dose of medicament is delivered into the patient. At this point, the tags 7A reach recesses 13 cut into the plunger housing 6 whereupon they are able to spring radially outwardly into those recesses (as illustrated in FIGS. 5 and 6). An audible click may be emitted which indicates to the user that the injection is complete. In addition, the user may "feel" that the injection is complete as a result of the tags 7A locating in recesses 13.

The outward movement of the tags 7A means that the "hammer head" shape is no longer in contact with the enlarged head 8A of the plunger 8 and therefore the plunger 8 is no longer driven forward by the ram 4 and tags 7A. The plunger housing 7 may continue further forward until an end stop is reached.

Figure 7:
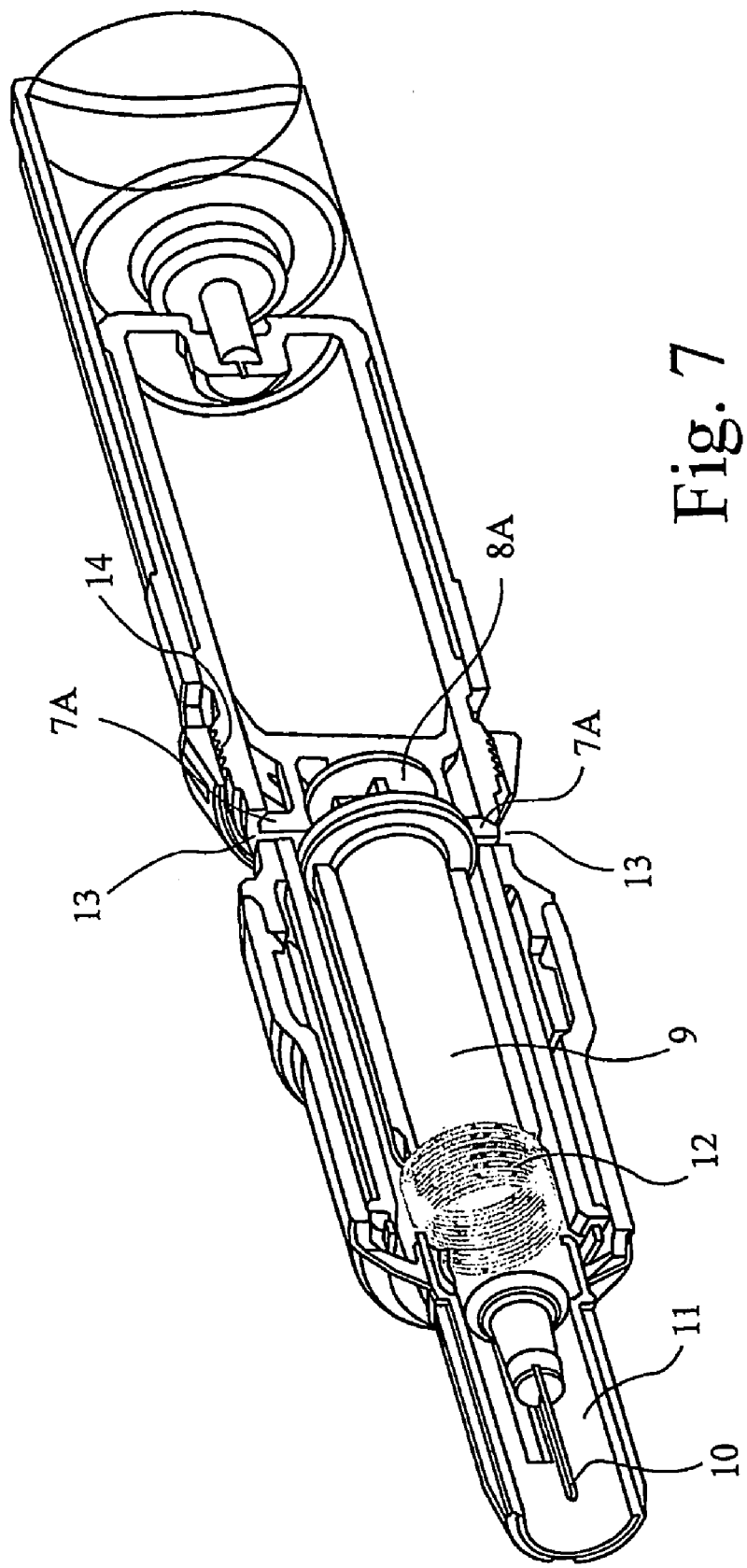
Figure 8:
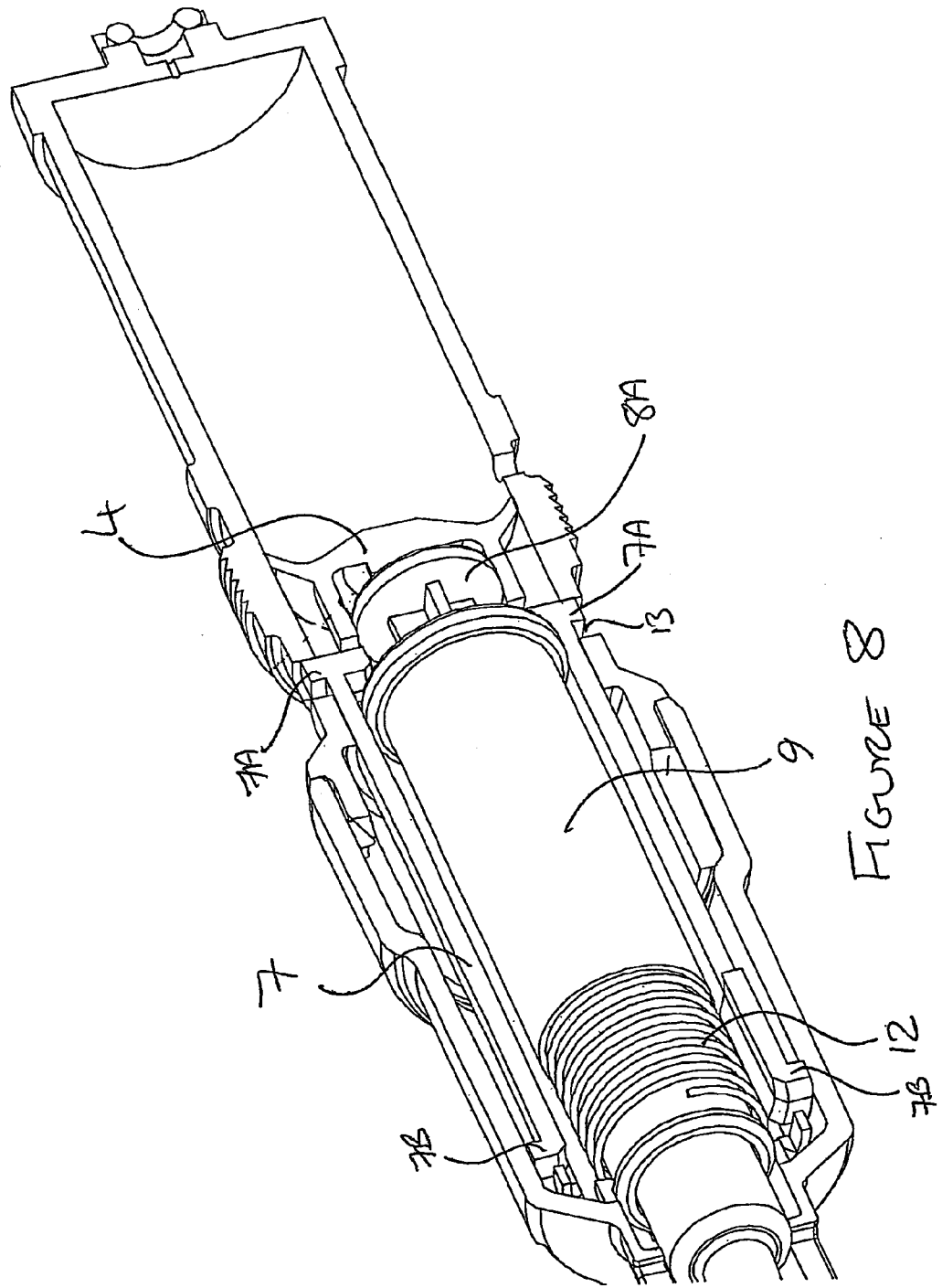

The final stage in the operation of the device is illustrated in FIGS. 7 and 8. With the tags 7A located within recesses 13, neither the plunger 8 nor the barrel 9 is impeded by any part of the plunger housing 7. Therefore the spring 12, which had been compressed by the forward motion of the barrel 9, urges the barrel 9 and hence the plunger 8 backwards until the ram 4 prevents further backward movement thereof. The backward movement is sufficient to cause the needle 10 to retract into the nozzle 11 so that it is no longer visible to the user and safe from the risk of causing a needle-stick injury. The used injection device can then be safely disposed of.

Blow-back is prevented by the provision of serrations 14 which guide the relative movement of the chamber housing 6 and the outermost housing. These serrations only permit relative movement in one direction, i.e. the chamber housing 6 moving forward with respect to the outermost housing.

Figure 9:
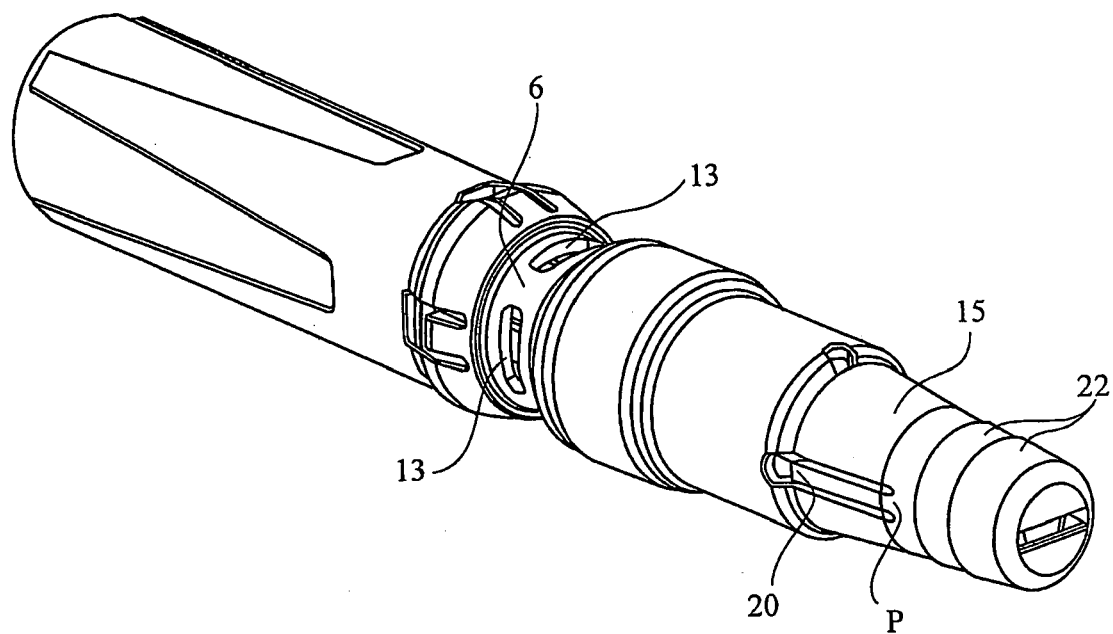
FIG. 9 is a perspective view of the device, including the needle cover.
Figure 10:
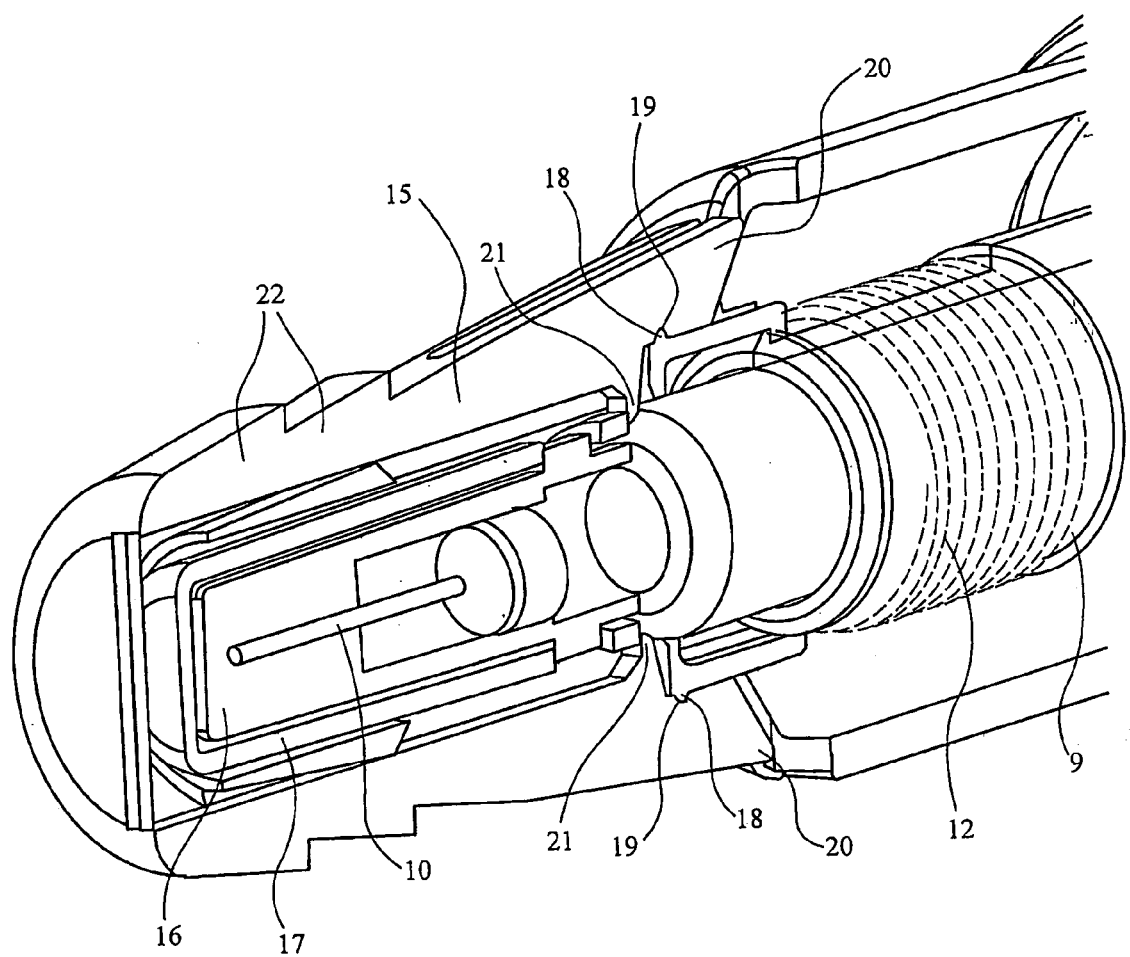
FIG. 10 is perspective view, partly in section, showing detail of the needle cover.

FIG. 9 is a perspective view of the injection device which, in this Figure, includes a needle cover 15. The needle cover is shown in further detail in FIGS. 10 and 11 and is used to protect the needle end of the injection device during transit, storage and before use to deliver an injection. The needle cover 15 has the further advantage of preventing accidental or unintended activation of the device, as it is not possible to fire the device with the needle cover 15 in place.

Regulations require that the needle (which is in direct communication with the medicament in the barrel) is sealed from the outside environment before use. This is achieved by providing protection in the form of a rubber moulding 16 which covers the end of the needle, the rubber moulding 16 being surrounded by a nylon sheath 17. The rubber moulding and nylon sheath (the "needle protection") are fixed with respect to one another by a friction fit between one or more protrusions 16A on the rubber moulding and a corresponding one or more recesses 17A in the nylon sheath.

The configuration of the needle protection depends upon the type of needle/barrel/plunger ("syringe assembly") employed in the injection device. It is envisaged that the injection device of the present invention could be assembled around a standard syringe assembly of known type (the selection thereof depending upon the required dose range, the type of medicament to be administered etc, for example). Different syringe assemblies may be supplied with slightly differing needle protection.

The nylon sheath and rubber moulding are firmly fixed on the needle 10 and it is difficult, if not impossible, for a patient to pull them from the needle using his/her fingers alone because of their position inside the nozzle 11. Therefore an outer needle cover 15 is provided which not only improves the aesthetic appearance of the injection device, before use, but also serves the function of facilitating the removal of the nylon sheath and rubber moulding.

The needle cover 15 is releasably retained on the front end of the injection device by the fit of annular protrusions 18 on part of the device housing with grooves 19 on the interior of the needle cover. The protrusions 18 and corresponding grooves 19 preferably extend around two equally opposed 60° portions of the circumference of the nozzle 11.

The grooves 19 are located on one or more (preferably equally spaced) flexible legs. 20 which are flexible compared to the rest of the needle cover 15, about point P shown in FIG. 9. Forward of each groove 19 is provided an inwardly projecting tab 21 on each flexible leg 20. Each tab 21 abuts the rear of the nylon sheath 17.

Figure 11:
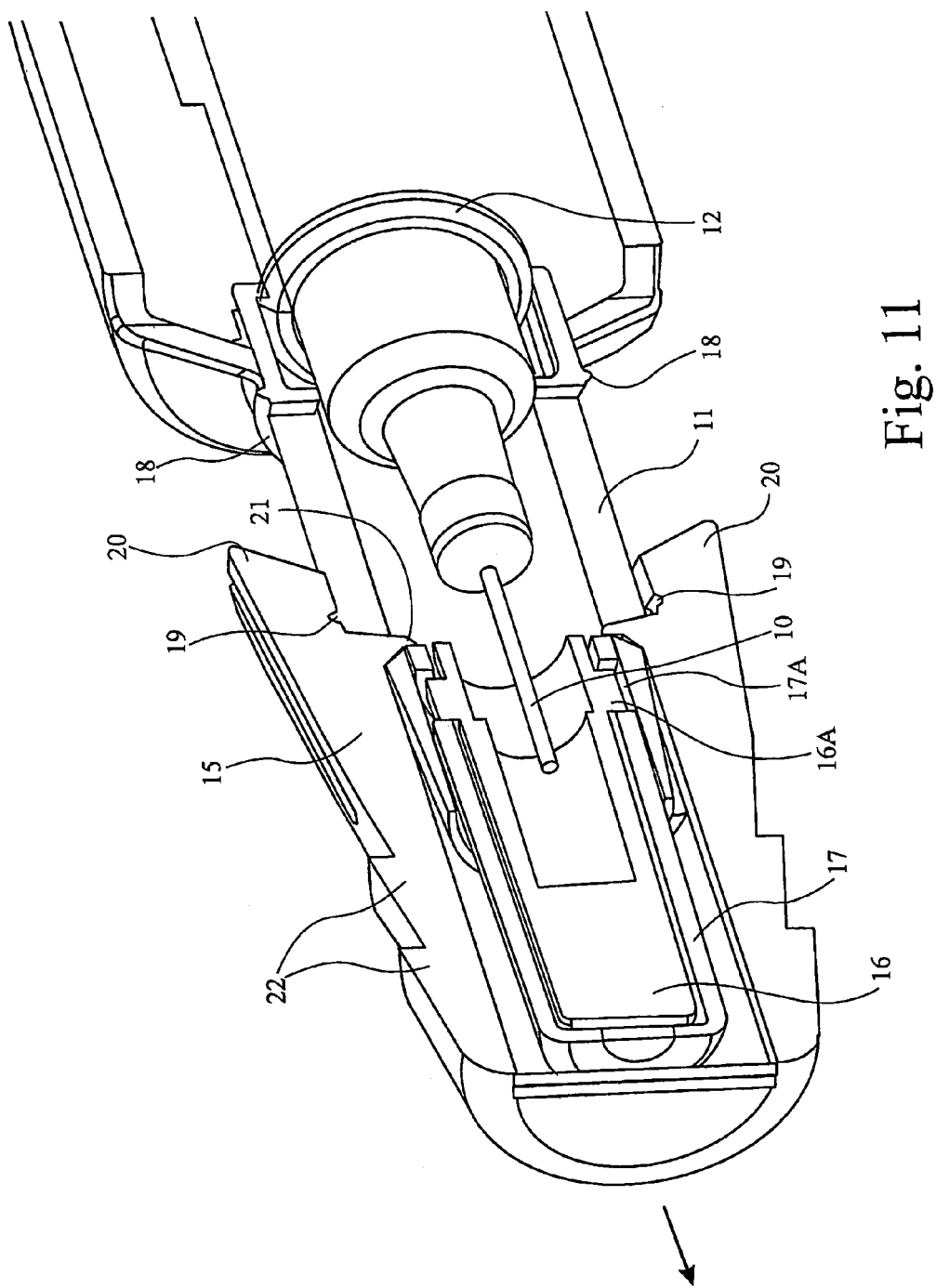
FIG. 11 is perspective view, partly in section, showing detail of the needle cover part way through being removed from the injection device.
Figure 12:
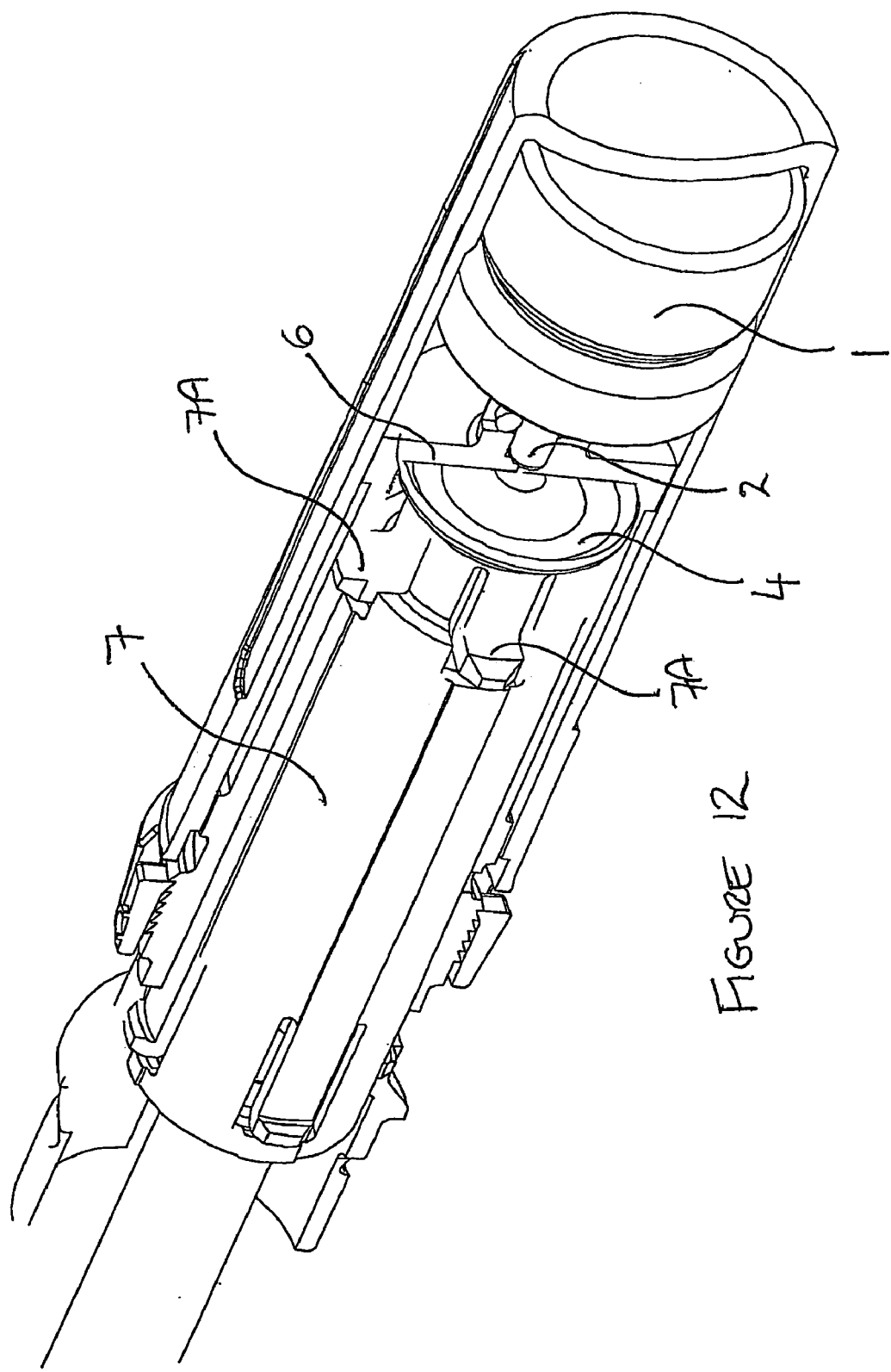
FIG. 12 is a schematic view showing the relationship between tags 7A and ram 4, in one embodiment of the invention.

Turning now to FIG. 11, when it is desired to remove the needle cover 15 from the device, the user grips the needle cover, preferably in a region having texture or other grip-improving means 22, and pulls in the direction indicated by the arrow in FIG. 11. The flexibility of the legs 20 permits the needle cover to ride over the protrusions 18, disengaging them from the grooves 19. The flexibility of the legs 20 is minimal enough not to cause the tabs 21 to become disengaged from the rear of the nylon sheath 17.

Therefore, as the needle cover 15 is pulled in the direction indicated by the arrow, the tabs 21 are urged against the rear of the nylon sheath 17 and sufficient force can be applied thereby to disengage the needle 10 from the rubber moulding 16. In this way, the entire moulding 16, nylon sheath 17 and needle cover 15 can be removed from the injection device and discarded, so that the injection device is then ready to use.

Other types of needle cover 15 may be envisaged, suited to the particular type of syringe assembly used in the device, for example that described below with reference to FIG. 25 et seq.

FIGS. 13 and 14 show more detail of an embodiment of the inner housing 7 in which the ram 4 is integral with the housing 7.

The inner housing is injection moulded as a single piece having four orthogonally placed tags at each end thereof. Each tag 7A, 7B is at the end of a resiliently flexible leg, cut out of the material of the housing 7, so that each leg (and its respective tag) is able to flex radially with respect to the remainder of the housing 7.

The rear part of the inner housing 7 constitutes the equivalent of the ram 4 described above. The ram is provided with an annular groove or recess 4A, into which the ball bearings 42 locate.

The inner housing 7 may also be provided with one or more guide means which, in the illustrated embodiment, take the form of elongate protrusions 7C. These protrusions 7C cooperate with corresponding recesses on the interior surface of the outer housing 30 so that, in use, relative axial movement of the inner and outer housings is guided.

A spring-powered embodiment of the injection device is described below with reference to FIG. 15 et seq.

In this embodiment, there is a generally cylindrical outer housing 30 extending all the way from the rear of the device to the needle cover 15. The gas cylinder 1 and valve 2 are replaced by a spring-powered energy source. Referring particularly to FIG. 16, a spring 40 is provided under compression at the rear of the device, intermediate the rear of a spring housing 41 and the ram 4. The spring 40 is retained in its compressed condition by means of one or more ball bearings 42 sitting in annular recess 4A on the ram 4, the ball bearings 42 being wedged against the outer housing 30 and located in apertures 41C at the front of the spring housing 41. The spring housing 41 interacts with the back of the outer housing 30 by means of an arrangement illustrated in FIG. 17.

The spring housing 41 is provided with elongate slots 41B and generally circular apertures 41C. The corresponding part of the outer housing is provided with elongate protrusions 30B on the interior surface thereof, which fit into the slots 41B as illustrated in FIG. 17. The ball bearings 42 (not shown in FIG. 17) fit through the circular apertures 41C.

In FIG. 15 it can be seen that the front end of the outer housing 30 is in close relation, or abutting, the needle cover 15. This substantially prevents any forward movement of the outer housing 30 in relation to the spring housing 41 and other components.

In FIG. 18, the needle cover has been removed and it is now possible to place the device against the user's leg (or other injection site) ready to initiate an injection.

FIG. 19 shows the front part of the device at this stage, in more detail.

Referring now to FIGS. 19 and 20, the front part of the device is shown in more detail. At the front of the outer housing 30, there are provided two annular grooves 30A and 30A' on the interior surface thereof. A spacer part S0 is fixed with respect to the nozzle 11 and other components internal of the outer housing 30. The spacer part 50 is provided with an exterior annular protrusion 51 which initially locates in the forwardmost groove 30A.

The leading edge of forwardmost groove 30A is generally blunt so that location of protrusion 51 therein (as illustrated in FIG. 19) inhibits the user from pulling the outer housing 30 rearwardly off the spring housing 41 et al, which might dangerously expose the internal components of the device. It is difficult for a user to apply sufficient rearward force to cause the protrusion. 51 to ride over the blunt leading edge.

The trailing edge of the forwardmost groove 30A and both edges of the groove 30A' are curved or tapered.

To initiate an injection, the user grasps the outer housing 30 and effects forward movement of the outer housing 30 in relation to the spring housing 41. As shown in FIG. 20, the forward movement causes the protrusion 51 to disengage from the forwardmost groove 30A and, as the outer housing 30 moves forward with respect to the spacer 50, the protrusion 51 engages in the rearmost groove 30A'.

Referring now to FIGS. 18 and 21, the relationship between the ram 4, ball bearings 42 and spring housing 41 is described in more detail. In the first position, shown in FIG. 18, the ball bearings 42 sit in the annular groove 4A in the ram 4 and are wedged in place in the apertures 41C at the front of the spring housing 41.

FIG. 21 shows the device in the same condition as in FIG. 20 i.e. wherein forward movement of the outer housing in relation to the spring housing has caused the protrusion 51 to be engaged in the rearmost groove 30A'.

In this position, the spring housing 41 has moved closer to the rear bf the outer housing 30. This relative axial movement is sufficient to cause the apertures 41C to retreat back past an undercut area 30A" inside the outer housing 30. The ball bearings 42 are now free to move radially out of the apertures 41C and into said undercut area 30A", out of engagement with the ram 4. The ram 4 is now free to travel forwards in the direction indicated by the arrow in FIG. 21, under the power of the spring 40.

The forward-moving ram 4 causes the inner housing 7 to deliver the injection as previously described. This is illustrated in FIG. 21 (Stage 2 as previously described) and FIG. 22 (Stage 3 as previously described).

FIG. 23 shows the position in which the injection has been fully delivered and the needle caused to retract back inside the nozzle (final stage as previously described).

In an alternative embodiment (not illustrated), the ball bearings 42 are replaced by a living joint, moveable into undercut area 30A" and out of engagement with the ram 4.

In another embodiment (not illustrated), the protrusion 51 and grooves 30A, 30A' are replaced or supplemented by a ratchet arrangement described hereafter. A spring housing is provided which has a substantially square cross-section. A portion of the inside of the outer housing 30 is correspondingly shaped with a square cross-section so that the spring housing and outer housing closely fit together but relative axial movement between them is possible. Relative rotational movement between them is substantially prevented by the square cross-section. At least one surface of the square cross-section spring housing is provided with a plurality of barbs, protrusions, ratchet teeth or the like which cooperate with an inwardly-depending protrusion or tag on the inside of the outer housing.

The ratchet arrangement performs the same function as protrusion 51 and grooves 30A, 30A' i.e. to control forward movement of the outer housing 30 in relation to the spring housing 41. The ratchet arrangement may provide further advantages, for example:

Improved strength;
Rotational alignment between spring housing and outer housing;
Improved resistance to rearward force generated by the user pushing the device hard into the injection site;
Improved resistance to the user pulling the outer housing rearwardly off the device, the ratchet teeth permitting forward movement of the outer housing only;
Improved defining of the relative axial position of the outer housing and internal components of the device.

Alternative embodiments are envisaged in which, instead of a square cross-section, the spring housing has at least one flat surface on which the barbs, protrusions, ratchet teeth or the like are disposed; the remainder of the spring housing may be of any cross-sectional shape so long as the inside of the outer housing is correspondingly shaped.

Other modifications to the injection device are illustrated in FIG. 13 et seq which are equally applicable to the gas-powered embodiment described earlier.

The barrel 9 may be provided with a transparent window 9a which, in use, is aligned with a window 32 in the outer housing (see FIG. 24) so that the liquid medicament is visible. During the injection. (i.e. during firing of the injection device), the plunger housing 7 becomes visible as it moves forwardly intermediate the barrel 9 and outer housing. As the plunger housing 7 moves forwardly, it progressively obscures the window 9a thus giving a visual indication to the user of the progress of the injection. The window 9a may be completely obscured by the plunger housing 7 when the injection is complete. The plunger housing 7 may be brightly coloured e.g. red to increase its visibility through the window 30.

It is observed that plastics of the type which may be used to form the plunger housing 7 will, over time, tend to gain a memory of the position in which they are stored. It is essential for operation of the device that the tags 7A spring properly into and out of engagement with the enlarged head 8A of the plunger. Therefore, as visible in FIG. 18, a tapered surface 31 is provided on the interior of the outer housing 30. This enables the tags 7A to be stored in their "relaxed" position, i.e. sprung radially-outwardly to abut the outer housing 30, as illustrated in FIG. 18.

When an injection is initiated as shown in FIG. 21, the forward movement of the outer housing 30 in relation to the plunger housing 7 causes the tags 7A to ride up the tapered surface 31 and into engagement with the enlarged head 8A of the plunger.

When the plunger housing 7 has moved forward sufficiently for tags 7A to reach recesses 13, the tags, 7A will have an increased tendency to spring outwardly into the position in which they had been previously stored, ensuring efficient operation of the device.

FIGS. 26 and 27 show an alternative embodiment of the needle cover 15. Like parts are given the same reference numerals as in FIG. 11. In the FIG. 26 embodiment, the needle cover 15 is releasably retained on the front end of the injection device by the fit of protrusions 11A on the exterior of the nozzle 11 with corresponding recesses on the interior of the needle cover 15.

The protrusions 11A may take the form of a single helical protrusion as illustrated in FIG. 25, or alternatively several discrete protrusions may be used.

At the front end of the needle cover 15 is a floating rivet 35 which has rearwardly directed barbed fingers 36 which pass through an aperture in the front end of the sheath 17.

The protrusions 11A the barbed fingers 36 and the interaction of the nozzle with the needle cover 15 at surface 15A mean that the nozzle 11 and associated components are prevented from moving axially with respect to the housing 30 in the situation illustrated in FIG. 26. This means that the device cannot be inadvertently fired whilst the needle cover 15 is still in place.

When it is desired to remove the needle cover 15 from the device, the user grips the needle cover and pulls in the direction indicated by the arrow in FIG. 26, using a twisting motion to cause the needle cover to ride along the nozzle guided by the helical protrusion 11A.

The floating rivet 35 allows the needle cover 15 to be twisted in order for it to move along helical protrusion 11A, but the sheath 17 does not twist and is simply pulling axially off the needle. This means there is no risk of damage to the needle 10 caused by twisting forces.

As the needle cover 15 is pulled in the direction indicated by the arrow, the barbed fingers 36 pull the sheath 17 with sufficient force to disengage the needle 10 from the rubber moulding 16. In this way, the entire moulding 16, nylon sheath 17 and needle cover 15 can be removed from the injection device and discarded, so that the injection device is then ready to use. Removal of the needle cover 15 has the second function of allowing the nozzle etc to be free to move axially with respect to the housing 30, which enables the device to be fired as described above.

When the end of the protrusion 11A is reached, the needle cover 15 is disengaged from the nozzle 11 as illustrated in FIG. 27.

A further embodiment of the present invention is envisaged wherein the needle is exposed upon removal of the needle cover 15. Such an embodiment may be suitable for users where needle-phobia is not a concern and where the complexity (and hence cost) of the device can be reduced by eliminating the need for the first stage (i.e. the forward movement of the needle out of the nozzle 11). The optional needle cover 15 may be omitted from such an embodiment. As mentioned above, it is possible that the injection device of the present invention may be supplied separately from and then assembled around a standard syringe assembly (needle/barrel/plunger) of known type.

In a further development, it is envisaged that it would be readily possible to adapt the device of the present invention to be operable with a standard cartridge or vial of medicament (Containing a volume of medicament from which several doses of user-defined volume can be provided) instead of a syringe assembly. In such case the needle could be removable and replaceable so that the device could be reused until the medicament cartridge is empty.

The invention claimed is:

1. An injection device comprising an outer housing inside which is located:
    a barrel for holding a volume of a medicament;
    a needle at one end of the barrel, the needle and barrel being such that at least part of the needle is axially moveable in and out of the outer housing but is biased to be normally wholly inside the housing;
    a plunger, axially moveable within the barrel;
    an inner housing at least partially intermediate the outer housing and at least one of the barrel and plunger; and
    an energy source in communication with the inner housing, wherein the inner housing is moveable by the energy source between three positions, namely:
    a first position in which a plurality of radially flexible tags formed as part of the inner housing are in communication with the barrel such that, in use, the plunger and the barrel are movable by the inner housing axially so as to move at least part of the needle out of the outer housing;
    a second position in which one or more of the radially flexible tags formed as part of the inner housing is in communication with the plunger but not the barrel such that, in use, the plunger is movable axially into the barrel so as to expel medicament through the needle; and
    a third position in which one or more of the radially flexible tags formed as part of the inner housing is in communication with neither the plunger nor the barrel such that, in use, the plunger and barrel are able to retract in order to retract the needle into the outer housing.

2. An injection device as claimed in claim 1 further comprising a spring housing intermediate the outer housing and the inner housing.

3. An injection device as claimed in claim 1 wherein one or more of the radially flexible tags is located at the end of a resiliently flexible leg.

4. An injection device as claimed in claim 1, wherein one or more of the radially flexible tags are rear tags that are situated at a rear end of the inner housing and are moveable radially into and out of communication with the plunger.

5. An injection device as claimed in claim 2, wherein in said second position the radially flexible tags are biased radially inwardly into communication with the plunger, preferably by communication with the spring housing.

6. An injection device as claimed in claim 1, wherein the radially flexible tags are stored in a relaxed condition, before initiating an injection.

7. An injection device as claimed in claim 4, wherein each rear tag is moveable out of communication with the plunger when aligned with a corresponding recess in a spring housing.

8. An injection device as claimed in claim 4, wherein each rear tag is substantially T-shaped.

9. An injection device as claimed in claim 1, wherein one or more of the radially flexible tags are forward tags that are situated at a forward end of the inner housing and are moveable radially into and out of communication with the barrel.

10. An injection device as claimed in claim 9 wherein the forward tags are biased radially inwardly into communication with the barrel, preferably by communication with a spring housing.

11. An injection device as claimed in claim 9, wherein the forward tags are stored in a relaxed condition, before initiating an injection.

12. An injection device as claimed in claim 9, wherein each forward tag is moveable out of communication with the barrel when aligned with a corresponding recess in the outer housing.

13. An injection device as claimed in claim 9, wherein each forward tag is substantially L-shaped.

14. An injection device as claimed in claim 1, wherein the energy source is a compressed gas.

15. An injection device as claimed in claim 1, wherein energy source is a spring.

16. An injection device as claimed in claim 1, further including means for allowing the inner housing to move axially only forward with respect to the outer housing.

17. An injection device as claimed in claim 16 wherein the means for allowing the inner housing to move axially only forward with respect to the outer housing is an arrangement of serrations, barbs, ratchet teeth or the like intermediate the housings.

18. An injection device as claimed in claim 1, further comprising guide means for guiding, in use, the relative axial movement of the spring and outer housings, the guide means preferably comprising one or more protrusions on the spring housing which, in use, cooperate with corresponding recesses on an interior surface of the outer housing.

19. An injection device as claimed in claim 1, wherein the needle is biased to be normally wholly inside the housing by means of a spring intermediate the barrel and the outer and/or spring housing.

20. An injection device as claimed in claim 1, wherein the needle is removable from the device.

21. An injection device as claimed in claim 1, wherein the needle, barrel and plunger are removable from the device.

22. An injection device as claimed in claim 1, further including a removable needle cover which protects the needle during storage before use.

23. An injection device as claimed in claim 22 wherein the needle cover includes means for pulling a protective rubber sheath from the needle when the needle cover is removed from the device.

24. An injection device as claimed in claim 23 wherein the pulling means includes a floating rivet intermediate the needle cover and the protective rubber sheath, whereby twisting forces applied to the needle cover are substantially prevented from being transmitted to the rubber sheath.

25. An injection device as claimed in claim 22, wherein the presence of the needle cover on the device serves as a safety lock, substantially preventing relative forward movement of the outer housing.

26. An injection device as claimed in claim 1, further comprising a viewing window in the barrel aligned with a viewing window in the outer housing such that the medicament can be viewed by a user prior to an injection taking place.

27. An injection device as claimed in claim 26 wherein, in use during an injection, the inner housing moves intermediate the viewing window in the outer housing and the barrel so as to obscure the window in the barrel from the user's view.

28. An injection device as claimed in claim 1, further comprising means for emitting an audible and/or physical indication to a user that the injection is complete.

29. An injection device comprising an outer housing inside which is located:
a barrel for holding a volume of a medicament;
a needle at one end of the barrel, the needle and barrel being such that at least part of the needle is axially moveable in and out of the outer housing but is biased to be normally wholly inside the housing;
a plunger, axially moveable within the barrel;
an inner housing intermediate at least a portion of the outer housing and at least a portion of at least one of the barrel and plunger; and
an energy source in communication with the inner housing, wherein the inner housing is moveable by the energy source between two positions, namely:
a first position in which one or more radially flexible tags formed as part of the inner housing are in communication with the barrel such that, in use, the plunger and the barrel are movable axially into the barrel to expel medicament through the needle;
a second position in which one or more of radially flexible tags formed as part of the inner housing are in communication with neither the plunger nor the barrel such that, in use, the plunger and barrel are able to retract in order to retract the needle into the outer housing.

30. An injection device comprising an outer housing adapted to receive:
a barrel for holding a volume of a medicament;
a needle at one end of the barrel, the needle and barrel being such that at least part of the needle is axially moveable in and out of the outer housing but is biased to be normally wholly inside the housing; and
a plunger, axially moveable within the barrel, wherein the injection device further comprises:
an inner; and
an energy source in communication with the inner housing, wherein the inner housing is moveable by the energy source between three positions, namely
a first position in which one or more radially flexible tags formed as part of the inner housing are in communication with the barrel such that, in use, the plunger and the barrel are movable axially so as to move at least part of the needle out of the outer housing;
a second position in which one or more of radially flexible tags formed as part of the inner housing are in communication with neither the plunger nor the barrel such that, in use, the plunger is movable axially into the barrel so as to expel medicament through the needle, and;
a third position in which the radially flexible tags formed as part of the inner housing are in communication with neither the plunger nor the barrel such that, in use, the plunger and barrel are able to retract in order to retract the needle into the outer housing.

31. An injection device as claimed in claim 29 comprising a spring housing intermediate the outer housing and the inner housing.

* * * * *

UNITED STATES PATENT AND TRADEMARK OFFICE
CERTIFICATE OF CORRECTION

PATENT NO. : 7,645,265 B2 Page 1 of 1
APPLICATION NO. : 10/597379
DATED : January 12, 2010
INVENTOR(S) : Kevin Stamp It is certified that error appears in the above-identified patent and that said Letters Patent is hereby corrected as shown below:

Claim 30, column 14, line 37, the term "an inner" should be changed to -- an inner housing --.

Signed and Sealed this

Eighteenth Day of May, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,645,265 B2 | Page 1 of 1 |
| APPLICATION NO. | : 10/597379 | |
| DATED | : January 12, 2010 | |
| INVENTOR(S) | : Kevin Stamp | |

It is certified that error appears in the above-identified patent and that said Letters Patent is hereby corrected as shown below:

On the title page, item (*) Notice should read:

Subject to any disclaimer, the term of this patent is extended or adjusted under 35 U.S.C. 154(b) by 386 days.

Signed and Sealed this

Twenty-fourth Day of August, 2010

David J. Kappos
*Director of the United States Patent and Trademark Office*